(12) United States Patent  
Green, II et al.

(10) Patent No.: US 8,641,598 B2
(45) Date of Patent: Feb. 4, 2014

(54) ORGAN MANIPULATOR APPARATUS

(75) Inventors: Harry Leonard Green, II, Anacortes, WA (US); Jon M. Tanaka, San Jose, CA (US); Edward A. Pineda, San Jose, CA (US); Dwight P. Morejohn, Davis, CA (US); Liming Lau, Mountain View, CA (US); John P Lunsford, San Carlos, CA (US); Robert Mosley, San Jose, CA (US); Joshua Wallin, San Jose, CA (US); Iris Leon Corbin, Redwood City, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 1392 days.

(21) Appl. No.: 12/338,471

(22) Filed: Dec. 18, 2008

(65) Prior Publication Data

US 2009/0299131 A1 Dec. 3, 2009

Related U.S. Application Data

(63) Continuation of application No. 10/615,007, filed on Jul. 8, 2003, now Pat. No. 7,479,104.

(51) Int. Cl.
*A61F 13/00* (2006.01)
(52) U.S. Cl.
USPC .......................................................... 600/37
(58) Field of Classification Search
USPC ..................................... 600/37; 128/897, 898
See application file for complete search history.

(56) References Cited

U.S. PATENT DOCUMENTS

| 452,131 | A | | 5/1891 | Haughawout |
| 810,675 | A | | 1/1906 | Richter |
| 1,706,500 | A | | 3/1929 | Smith |
| 2,082,782 | A | | 6/1937 | Allen |
| 2,296,793 | A | | 9/1942 | Kirschbaum |
| 2,590,527 | A | | 3/1952 | Fluck |
| 2,693,795 | A | | 11/1954 | Grieshaber |
| 2,798,757 | A | * | 7/1957 | Jackson ........................ 294/184 |

(Continued)

FOREIGN PATENT DOCUMENTS

| DE | 3138589 A1 | 4/1983 |
| DE | 9004513 | 6/1990 |

(Continued)

OTHER PUBLICATIONS

C.W. Akins et al., "Preservation of Interventricular Septal Function in Patients Having Coronary Artery Bypass Grafts Without Cardiopulmonary Bypass," American Heart Journal, vol. 107, No. 2 Feb. 1984, pp. 304-309.

(Continued)

*Primary Examiner* — Samuel Gilbert
(74) *Attorney, Agent, or Firm* — Law Office of Alan W Cannon

(57) ABSTRACT

Organ manipulation devices for atraumatically grasping the surface of an organ and repositioning the organ to allow access to a location on the organ that would otherwise be substantially inaccessible. Methods of accessing a beating heart, retracting the heart using an organ manipulation apparatus, and stabilizing a surgical target area with a stabilizer. Both the organ manipulator and stabilizer are fixed to a stationary object which may be a sternal retractor. A system for performing beating heart coronary artery bypass grafting includes a sternal retractor, organ manipulator and stabilizer.

36 Claims, 21 Drawing Sheets

(56) References Cited

U.S. PATENT DOCUMENTS

| | | |
|---|---|---|
| 2,863,444 A | 12/1958 | Winsten |
| 3,361,133 A | 1/1968 | Kimberley et al. |
| 3,392,722 A | 7/1968 | Jorgensen |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jacobs |
| 3,807,406 A | 4/1974 | Rafferty et al. |
| 3,858,926 A | 1/1975 | Ottenhues |
| 3,882,855 A | 5/1975 | Schulte et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,052,980 A | 10/1977 | Grams et al. |
| 4,096,864 A | 6/1978 | Kletschka et al. |
| 4,217,890 A | 8/1980 | Owens |
| 4,226,228 A | 10/1980 | Shin et al. |
| 4,230,119 A | 10/1980 | Blum |
| 4,300,564 A | 11/1981 | Furihata |
| 4,306,561 A | 12/1981 | de Medinaceli |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,925,443 A | 5/1990 | Heilman et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,196,003 A | 3/1993 | Bilweis |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,348,259 A | 9/1994 | Blanco et al. |
| 5,363,882 A | 11/1994 | Chikama |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,484,391 A | 1/1996 | Buckman et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,632,746 A | 5/1997 | Middleman et al. |
| 5,651,378 A | 7/1997 | Matheny et al. |
| 5,662,300 A | 9/1997 | Michelson |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,795,291 A | 8/1998 | Koros et al. |
| 5,797,960 A | 8/1998 | Stevens et al. |
| 5,799,661 A | 9/1998 | Boyd et al. |
| 5,807,243 A | 9/1998 | Vierra et al. |
| 5,813,410 A | 9/1998 | Levin |
| 5,818,231 A | 10/1998 | Smith |
| 5,836,311 A | 11/1998 | Borst et al. |
| 5,864,275 A | 1/1999 | Ohashi et al. |
| 5,865,730 A | 2/1999 | Fox et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A | 5/1999 | Corey Jr. et al. |

(56) References Cited

U.S. PATENT DOCUMENTS

| | | |
|---|---|---|
| 5,906,607 A | 5/1999 | Taylor et al. |
| 5,908,378 A | 6/1999 | Kovacs et al. |
| 5,921,979 A | 7/1999 | Kovacs et al. |
| 5,927,284 A | 7/1999 | Borst et al. |
| 5,947,896 A | 9/1999 | Sherts et al. |
| 5,957,835 A | 9/1999 | Anderson et al. |
| 5,967,973 A | 10/1999 | Sherts et al. |
| 5,976,069 A | 11/1999 | Navia et al. |
| 5,984,864 A | 11/1999 | Fox et al. |
| 6,007,486 A | 12/1999 | Hunt et al. |
| 6,010,531 A | 1/2000 | Donlon et al. |
| 6,013,027 A | 1/2000 | Khan et al. |
| 6,015,378 A | 1/2000 | Borst et al. |
| 6,015,427 A | 1/2000 | Mueller et al. |
| 6,019,722 A | 2/2000 | Spence et al. |
| 6,027,476 A | 2/2000 | Sterman et al. |
| 6,029,671 A | 2/2000 | Stevens et al. |
| 6,032,672 A | 3/2000 | Taylor |
| 6,033,362 A | 3/2000 | Cohn |
| 6,036,641 A | 3/2000 | Taylor et al. |
| 6,042,539 A | 3/2000 | Harper |
| 6,050,266 A | 4/2000 | Benetti et al. |
| 6,110,187 A | 8/2000 | Donlon |
| 6,120,436 A | 9/2000 | Anderson et al. |
| 6,139,492 A | 10/2000 | Vierra et al. |
| 6,149,583 A | 11/2000 | Vierra et al. |
| 6,159,201 A | 12/2000 | Hamilton et al. |
| 6,183,486 B1 | 2/2001 | Snow et al. |
| 6,193,652 B1 | 2/2001 | Berky et al. |
| 6,210,323 B1 | 4/2001 | Gilhuly et al. |
| 6,213,940 B1 | 4/2001 | Sherts et al. |
| 6,213,941 B1 | 4/2001 | Beneti et al. |
| 6,231,585 B1 | 5/2001 | Takahashi et al. |
| 6,251,065 B1 | 6/2001 | Kochamba |
| 6,264,605 B1 | 7/2001 | Scirica et al. |
| 6,315,717 B1 | 11/2001 | Benetti et al. |
| 6,328,688 B1 | 12/2001 | Borst et al. |
| 6,334,843 B1 | 1/2002 | Borst et al. |
| 6,336,898 B1 | 1/2002 | Borst et al. |
| 6,338,712 B2 | 1/2002 | Spence et al. |
| 6,346,077 B1 | 2/2002 | Taylor et al. |
| 6,350,229 B1 | 2/2002 | Borst et al. |
| 6,361,493 B1 | 3/2002 | Spence et al. |
| 6,364,826 B1 | 4/2002 | Borst et al. |
| 6,371,906 B1 | 4/2002 | Borst et al. |
| 6,371,910 B1 | 4/2002 | Zwart et al. |
| 6,375,611 B1 * | 4/2002 | Voss et al. ............ 600/210 |
| 6,390,976 B1 | 5/2002 | Spence et al. |
| 6,394,948 B1 | 5/2002 | Borst et al. |
| 6,394,951 B1 | 5/2002 | Taylor et al. |
| 6,398,726 B1 | 6/2002 | Ramans et al. |
| 6,406,424 B1 | 6/2002 | Williamson et al. |
| 6,447,443 B1 | 9/2002 | Keogh et al. |
| 6,458,079 B1 | 10/2002 | Cohn et al. |
| 6,464,629 B1 | 10/2002 | Goodman et al. |
| 6,464,630 B1 | 10/2002 | Borst et al. |
| 6,468,265 B1 | 10/2002 | Evans et al. |
| 6,478,029 B1 | 11/2002 | Boyd et al. |
| 6,478,728 B1 * | 11/2002 | Wright ............ 600/37 |
| 6,478,729 B1 | 11/2002 | Rogers et al. |
| 6,482,151 B1 | 11/2002 | Vierra et al. |
| 6,494,211 B1 | 12/2002 | Boyd et al. |
| 6,503,245 B2 | 1/2003 | Palmer et al. |
| 6,506,149 B2 * | 1/2003 | Peng et al. ............ 600/37 |
| 6,537,212 B2 | 3/2003 | Sherts et al. |
| 6,558,314 B1 | 5/2003 | Adelman et al. |
| 6,565,508 B2 | 5/2003 | Scirica et al. |
| 6,589,166 B2 | 7/2003 | Knight et al. |
| 6,592,573 B2 | 7/2003 | Castaneda et al. |
| 6,602,183 B1 | 8/2003 | Levi et al. |
| 6,607,479 B1 | 8/2003 | Kochamba et al. |
| 6,610,008 B1 | 8/2003 | Spence et al. |
| 6,610,009 B2 | 8/2003 | Person |
| 6,641,604 B1 | 11/2003 | Adelman et al. |
| 6,676,597 B2 | 1/2004 | Guenst et al. |
| 6,733,445 B2 | 5/2004 | Sherts et al. |
| 6,743,169 B1 | 6/2004 | Taylor et al. |
| 6,764,444 B2 * | 7/2004 | Wu et al. ............ 600/206 |
| 6,890,292 B2 | 5/2005 | Kochamba et al. |
| 6,899,670 B2 | 5/2005 | Peng et al. |
| 6,902,523 B2 | 6/2005 | Kochamba et al. |
| 6,936,002 B2 | 8/2005 | Kochamba et al. |
| 7,018,328 B2 | 3/2006 | Mager et al. |
| 7,056,287 B2 | 6/2006 | Taylor et al. |
| 7,137,949 B2 | 11/2006 | Scirica et al. |
| 7,179,224 B2 | 2/2007 | Willis |
| 7,226,409 B2 | 6/2007 | Peng et al. |
| 7,326,173 B2 | 2/2008 | Guenst et al. |
| 7,338,434 B1 | 3/2008 | Haarstad et al. |
| 7,438,680 B2 | 10/2008 | Guenst et al. |
| 7,497,823 B2 | 3/2009 | Parihar et al. |
| 2002/0058856 A1 * | 5/2002 | Peng et al. ............ 600/37 |
| 2002/0161285 A1 | 10/2002 | Spence et al. |
| 2003/0139645 A1 * | 7/2003 | Adelman ............ 600/37 |

FOREIGN PATENT DOCUMENTS

| | | |
|---|---|---|
| DE | 4139695 A1 | 6/1993 |
| EP | 0 293 760 A2 | 12/1988 |
| EP | 0 293 760 A3 | 12/1988 |
| EP | 0 293 760 BI | 12/1988 |
| EP | 0 630 629 A1 | 5/1994 |
| EP | 0 668 058 A1 | 2/1995 |
| EP | 668 058 A1 | 8/1995 |
| EP | 0 820 721 A1 | 7/1997 |
| EP | 0 791 329 A1 | 8/1997 |
| EP | 0 791 330 A2 | 8/1997 |
| EP | 0 808 606 A1 | 11/1997 |
| EP | 0 919 193 A1 | 6/1999 |
| GB | 168216 | 9/1921 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 96/40354 | 12/1996 |
| WO | WO 97/10753 | 3/1997 |
| WO | WO 97/26828 A | 7/1997 |
| WO | WO 97/40738 | 11/1997 |
| WO | WO 97/40752 | 11/1997 |
| WO | WO 98/37814 | 9/1998 |
| WO | WO 98/49944 | 11/1998 |
| WO | WO 99/60929 | 12/1999 |
| WO | WO 99/60930 | 12/1999 |
| WO | WO 00/10466 | 3/2000 |
| WO | WO 01/17437 | 3/2001 |
| WO | WO 01/58362 A1 | 8/2001 |

OTHER PUBLICATIONS

Ancalmo, N. and J. L. Ochsner: "A Modified Sternal Retractor," Ann. Thorac, Surg. 21 (1976) 174.

Angelini, G.D., M.D. et al., "A Fiber-Optic Retractor for Harvesting the Internal Mammary Artery," Ann. Thorac. Surg. (1990; 50:314-5).

Angelini, G.D., M.D., "A Simple, Inexpensive Method of Heart Retraction During Coronary Artery Bypass Surgery," Ann. Thora. Surg 46:46-247, Aug. 1988.

Anstadt, M.P. MD et al., "Direct Mechanical Ventricular Actuation for Cardiac Arrest in Humans," Chest, vol. 100, No. 1, Jul. 1991, pp. 86-92.

Antinori, C. et al., "A Method of Retraction During Reoperative Coronary Operations Using the Favaloro Retractor," The Society of Thoracic Surgeons: 1989.

Archer, R. DO et al., "Coronary Artery Revascularization Without Cardiopulmonary Bypass," Texas Heart Institute Journal, vol. 11, No. 1, Mar. 1984, pp. 52-57

(56) References Cited

OTHER PUBLICATIONS

Arom, K.V., et al., "Mini-Sternotomy for Coronary Artery Bypass Grafting," The Annals of Thoracic Surgery 1996; 61:1271-2.
Ballantyne, C.M. et al. "Delayed Recovery of Severely 'Stunned' Myocardium With the Support of a Left Ventricular Assist Device after Coronary Artery Bypass Graft Surgery," Journal of the American College of Cardiology, vol. 10, No. 3, Sep. 1987, pp. 710-712.
Bedellino, M.M., et al., "The Cardiac Rag—Simple Exposure of the Heart," Texas Heart Institute Journal, vol. 15, No. 2, 1988, 134-35.
Beg, R.A. et al., "Internal Mammary Retractor," Ann Thorac, Surg., vol. 39, No. 1, Jan. 1985, pp. 286-287.
Benetti, F. J. et al., "Direct Coronary Surgery with Saphenous Vein Bypass Without Either Cardiopulmonary Bypass Graft or Cardiac Arrest," The Journal of Cardiovascular Surgery, vol. 26, No. 3, May-Jun. 1985, pp. 217-222.
Benetti, F. J. et al., "Direct Myocardial Revascularization Without Extracorporeal Circulation," Chest, vol. 100, No. 2, Aug. 1991, pp. 312-316.
Benetti, F. J., "Coronary Revascularization with Arterial Conduits via a Small Thoracotomy and Assisted by Thoracoscopy, Although Without Cardiopulmonary Bypass," Cor Europaeum 4 (1) 22-24 (1995).
Borst et al., "Coronary Artery Bypass Grafting Without Cardiopulmonary Bypass and Without Interruption of Native Coronary Flow Using a Novel Anastomosis Site Restraining Device ('Octopus')", JAAC vol. 27, No. 6, May 1996:1356-64.
C. Borst et al., entitled "Regional Cardiac Wall Immunobilization for Open Chest and Closed Chest Coronary Artery Bypass Grafting on the Beating Heart: The 'Octopus' Method," Circulation, (Oct. 15, 1995) vol. 92, No. 8 supplemental I,I-177.
Bugge, M., "A New Internal Mammary Artery Retractor," Thorac. Cardiovasc Surgeon 38, pp. 316-317 (1990).
Buffolo, E., et al., "Direct Myocardial Revascularization Without Cardiopulmonary Bypass," Thorac. Cardiovasc. Surgeon, 33 (1985) pp. 26-29.
Calafiore, A. M., et al., "Minimally Invasive Coronary Artery Bypass Grafting," The Annals of Thoracic Surgery, 62:1545-8, 1996.
Calvin, I. F. & Newman, D.C., "Circumflex Exposure Using a Cardiac Sling," Ann Thorac Surg 1990:49:833-4.
Campalani, G., M.D., et al., "A New Self-Retaining Internal Mammary Artery Retractor," J. Cardiovas. Surg. 28, 1987, pp. 347-348.
Chaux, A. and Blanche, C., "A New Concept in Sternal Retraction: Applications for Internal Mammary Artery Dissection and Valve Replacement Surgery," Ann. Thorac. Surg. 42, Oct. 1986, pp. 473-474.
Cohen, A.S., et al., "Mini-Sternotomy for Coronary Artery Bypass Grafting," The Annals of Thoracic Surgery 1996; 62:1884-85.
Cutler, B.S. and Cantelmo, N.L., "New Use for an Old Clamp," Archives of Surgery—vol. 115, 1136-37, Sep. 1980.
Delacroix-Chevalier Surgical Instruments, IMA Saving Packages Brochure.
DelRossi, A J and Lemole, GM, "A New Retractor to Aid in Coronary Artery Surgery," The Annals of Thoracic Surgery, vol. 36, No. 1, 101-102, Jul. 1983.
Donald, I., "Snake Flexible Arm" British Medical Journal, Oct. 19, 1968, p. 170.
English abstract for Russian Patent No. SU 938967.
Fanning, W. J. et al., "Reoperative Coronary Artery Bypass Grafting Without Cardiopulmonary Bypass," The Annals of Thoracic Surgery, vol. 55, No. 2, Feb. 1993, pp. 486-489.
Favaloro, R. G., et al. "Direct Myocardial Revascularization by Saphenous Vein Graft," The Annals of Thoracic Surgery, vol. 10, No. 2, Aug. 1970, pp. 97-111.
Fonger, J. D., et al., "Enhanced Preservation of Acutely Ischmenic Myocardium with Transeptal Left Ventricular Assist," The Annals of Thoracic Surgery, vol. 57, No. 3, Mar. 1994, pp. 570-575.
Gacioch, G. M., MD, et al., "Cardiogenic Shock Complicating Acute Myocardial Infarction: The Use of Coronary Angioplasty and the Integration of the New Support Device into Patient Management," Journal of the American College of Cardiology, vol. 19, No. 3, Mar. 1, 1992.

Green, GE., "Technique of Internal Mammary—Coronary Artery Anastomosis," The Journal of Cardiovascular Surgery, 78:455-79, 1979.
Grundeman et al., "Vertical Displacement of the Beating Heart by the Octopus Tissue Stabilizer: Influence on Coronary Flow", Ann Thorac Surg 1998; 65: 138-152.
Grundeman et al., "Hemodynamic Changes During Displacement of the Beating Heart by the Utrecht Octopus Method", Ann Thorac Surg 1997; 66:576-579.
Guzman, F. M.D., "Transient Radial Nerve Injury Related to the Use of A Self Retraining Retractor for Internal Mammary Artery Dissection," J. Cardiovasc. Surg. 30, 1989, pp. 1015-1016.
Hasan, R. I., et al., "Technique of Dissecting the Internal Mammary After Using The Moussalli Bar," European Journal of Cardio Thoracic Surgery, 4:571-572, 1990.
Itoh, Toshiaki, M.D., et al., "New Modification of a Mammary Artery Retractor," Ann. Thorac. Surg. 9, 1994; 57:1670-1.
Jansen et al., "Experimental Off-Pump Grafting of a Circumflex Brach via Sternotomy Using a Suction Device", Ann Thorac Surg 1997; 63:S93-6.
Jansen et al., "Off-Pump Coronary Bypass Grafting: How to Use the Octopus Tissue Stabilizer," Ann Thorac Surg 1998; 66:576-9.
Japanese Journal of Thoracic Surgery, vol. 42, No. 2, 1989.
Japanese Article "Heart Retractor".
Janke, W. H., "Heart Support for Coronary Bypas Surgery Involving the Circumflex Artery System." The Journal of Thoracic and Cardiovascular Surgery, pp. 883-884.
Kolessov, V.I., M.D., "Mammary Artery—Coronary Artery Anastomosis as Method of Treatment for Angina Pectoris," Thoracic and Cardiovascular Surgery, vol. 54, No. 4, Oct. 1967, pp. 535-544.
Kazama, S. et al., "Fabric Heart Retractor for Coronary Artery Bypass Operations," The Annals of Thoracic Surgery, 55:1582-3, 1993.
Kresh, J. Y., et al., "Heart-Mechanical Assist Device Interaction," Trans. Am. Soc. Artif. Intern. Organs, vol. XXXII, 1986, pp. 437-443.
Lavergne, et al., "Transcatheter Radiofrequency Ablation of Atrial Tissue Using a Suction Catheter," PACE, vol. 12, Jan. 1989, Part II, pp. 177-186.
Lonn, U., M.D., et al., "Coronary Artery Operation Supported by the Hemopump: An Experimental Study on Pigs," The Annals of Thoracic Surgery, vol. 58, No. 1, Jul. 1994, pp. 516-523.
Matsuura, A., et al., "A New Device for Exposing the Circumflex Coronary Artery," The Annals of Thoracic Surgery, 59:1249-50, 1995, pp. 1249-1250.
McGee, M. G.,et al., "Extended Clinical Support with an Implantable Left Ventricular Assist Device," Trans. Am. Soc. Artif. Intern. Organs, vol. XXXV, 1989, pp. 614-616
McKeown, P.P. et al., "A Modified Sternal Retractor for Exposure of the Internal Mammary Artery," Ann. Thorac. Surg. 32 (1981) 619.
Ochsner, J. L., et al., "Surgical Management of Diseased Intracavitary Coronary Arteries," The Annals of Thoracic Surgery, vol. 38, No. 4, Jul. pp. 356-362, Oct. 1984.
Parsonnet, V. MD, et al., "Graduated probes for Coronary Bypass Surgery," The Journal of Thoracic and Cardiovascular Surgery, vol. 68, No. 3, 424-26 (Sep. 1974)
Parsonnet, V. MD, et al., "Self—Retaining Epicardial Retractor for Aortocoronary Bypass Surgery," The Journal of Thoracic and Cardiovascular Surgery, 629-30 1979.
Pfister, A. J. M.D., et al., "Coronary Artery Bypass Without Cardiopulmonary Bypass," The Annals of Thoracic Surgery, vol. 54, No. 6, Dec. 1992, pp. 1085-1092.
Phillips, Steven J., M.D. et al., "A Versatile Retractor for Use in Harvesting the Internal Mammary Artery and Performing Standard Cardiac Operations," J. Thorac. Cardiovasc. Surg. (1989; 97:633-5).
Pilling Surgical Instruments, A Rusch International Company Brochure.
Pittman, John, M.D., et al., "Improved Visualization of the Internal Mammary Artery with a New Retractor System," Ann. Thorac. Surg., 1989; 48:869-70.
Riahi, M.,et al., "A Simple Technique and Device to Provide a Bloodless Operative Field in Coronary Artery Surgery Without Cross-Clamping the Aorta," The Journal of Thoracic and Cardiovascular Surgery, vol. 66, No. 6, Dec. 1973, pp. 974-978.

(56) References Cited

OTHER PUBLICATIONS

Richenbacher, W. E., MD, et al., "Current Status of Cardiac Surgery: A 40-Year Review," Journal of American College of Cardiology, vol. 14, No. 3, pp. 535-544.

Robicsek, F., "Aortic Spoon-Jaw Clamp for Aorto-Saphenous Vein Anastomosis," J. Card. Surg., 1995; 10:583-585.

Robinson, M. C., et al., "A Minimally Invasive Surgical Method for Coronary Revascularization—Preliminary Experience in Five Patients," Circulation, Oct. 15, 1995, vol. 92, No. 8, 1-176.

Rousou, J. et al., "Cardiac Retractor for Coronary Bypass Operations," Ann Thorac. Surg, 1991; 52:877-8.

Roux, D., M.D. et al., "Internal Mammary Artery Dissection: A Three Dimensional Sternal Retractor," J. Cardiovasc. Surg., 1989; 30:996-7.

Roux, D., M.D. et al., "New Helper Instrument in Cardiac Surgery," Ann. Thorac. Surg., 1989, 48:595-596.

Ruzevich, S. A., et al., "Long-Term Follow-Up of Survivors of Postcardiotomy Circulatory Support," Trans. Am. Soc. Artif. Intern. Organs, vol. XXXIV, 1988, pp. 116-124.

Scholz, K. H., et al., "Transfemoral Placement of the Left Ventricular Assist Device 'Hemopump' During Mechanical Resuscitation," Thoracic and Cardiovascular Surgeon, vol. 38 (1990) pp. 69-72.

Splittgerber et al., "Exposing the Circumflex Coronary Artery: The Heartflip Technique," Ann Thorac Surg. 1996;61:1019-20.

Stevens, et al., "Closed Chest Coronary Artery Bypass With Cardioplegic Arrest in the Dog." 67$^{th}$ Scientific Session, 238, 1-251.

Takahashi et al., "A New Instrument for Immobilization and Hemostasis During Minimally Invasive Direct Coronary Artery Bypass ('MIDCAB doughnut'): Experimental Study", J Card Surg 1997; 12:185-189.

Trapp W.G., "To Use or Not To Use the Pump Oxygenator in Coronary Bypass Operations," The Annals of Thoracic Surgery, vol. 19, No. 1, Jan. 1975, pp. 108-109.

Trapp, et al., "Placement of Coronary Artery Bypass Graft without Pump Oxygenator," Journal of the Society of Thoracic Surgeons and The Southern Thoracic Surgeons Assn. vol. 19, No. 1, Jan. 1975.

USSC Cardiovascular Thora-Lift™, United States Surgical Corporation, Norwalk Connecticut, Product Brochure.

Vincent, J.G., "A Compact Single Post Internal Mammary Artery Dissection Retractor," Eur. J. Cardio-Thor. Surg. 3 (1989) 276-277.

Westaby, S., "Coronary Surgery Without Cardiopulmonary Bypass," British Heart Journal vol. 73 pp. 203-205, 1995.

Westaby, S. et al., "Less Invasive Coronary Surgery: Consensus From the Oxford Meeting," The Annals of Thoracic Surgery, 62:924-31, 1996.

Zumbro, G. L. et al., "A Prospective Evaluation of the Pulsatile Assist Device," The Annals of Thoracic Surgery, vol. 28, No. 2, Aug. 1979, pp. 269-273.

* cited by examiner

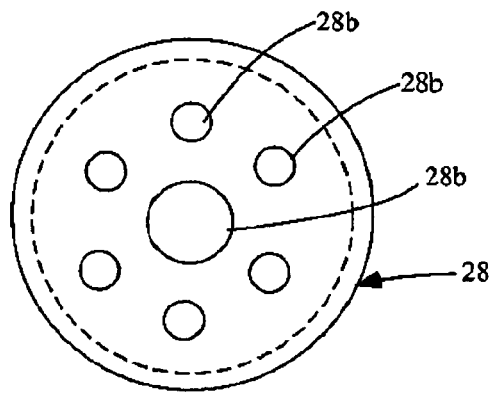
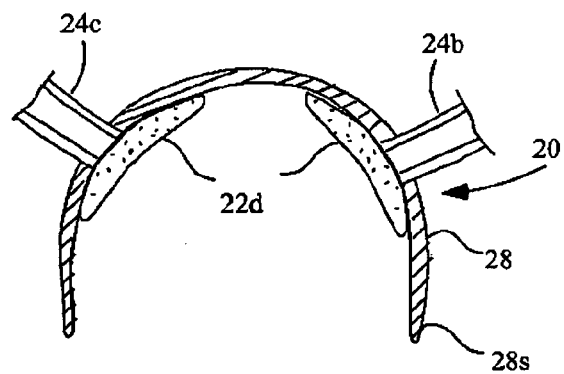
Fig. 9B  Fig. 10A
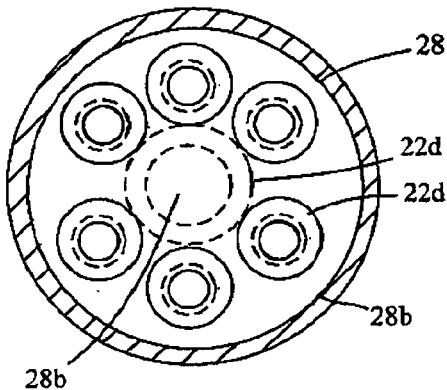
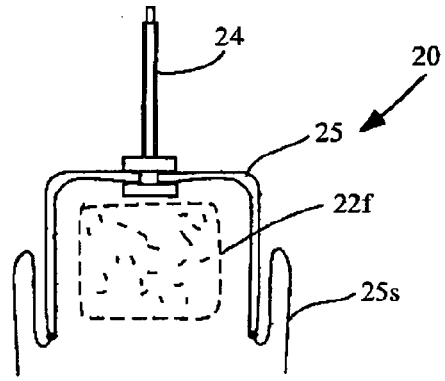
Fig. 10B  Fig. 11
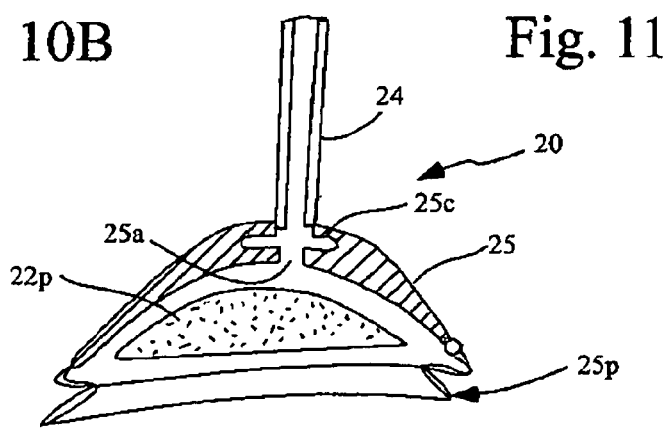
Fig. 12A

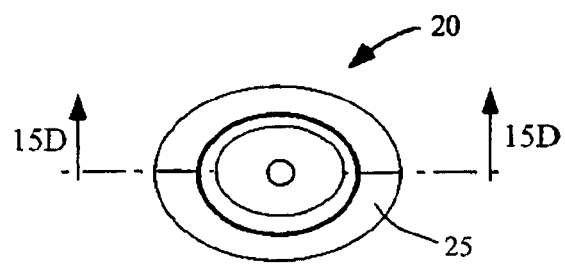
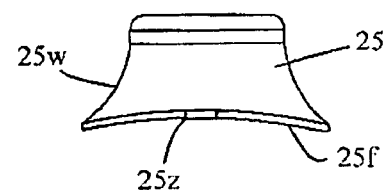
Fig. 15A    Fig. 15B
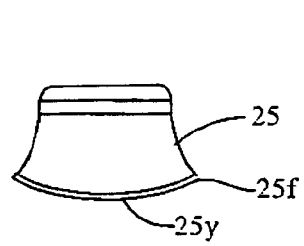
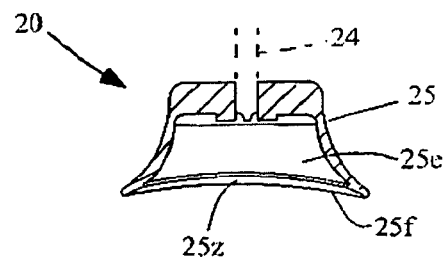
Fig. 15C    Fig. 15D

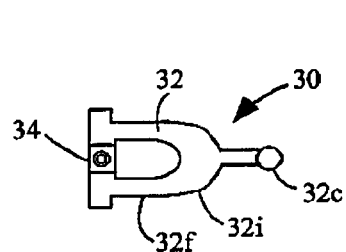
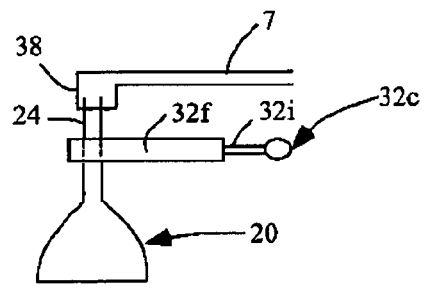
Fig. 17A    Fig. 17B
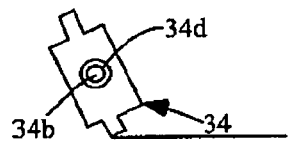
Fig. 17C
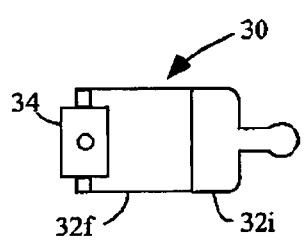
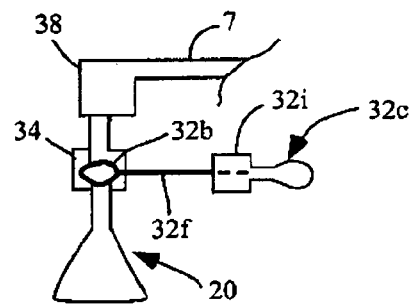
Fig. 18A    Fig. 18B
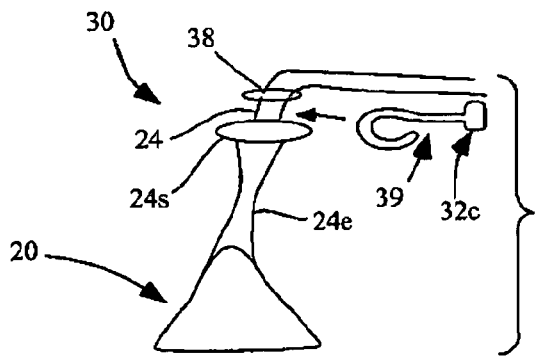
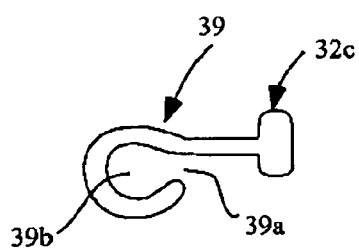
Fig. 19A    Fig. 19B

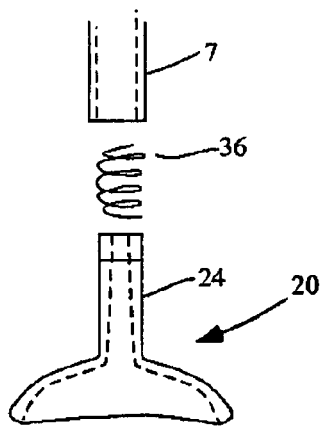 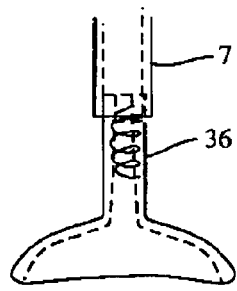 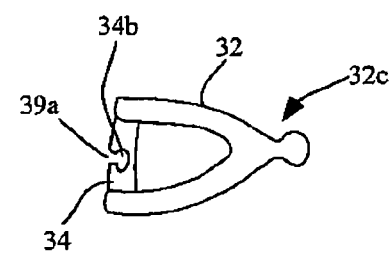
Fig. 27A  Fig. 27B  Fig. 27C
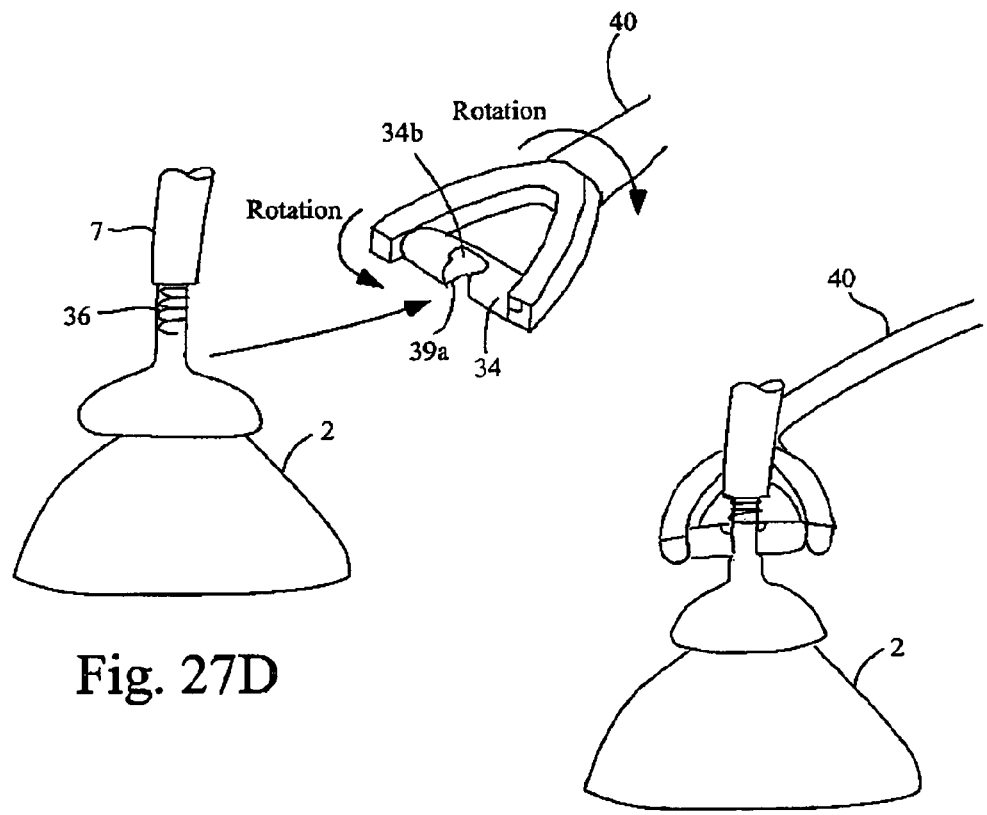
Fig. 27D
Fig. 27E

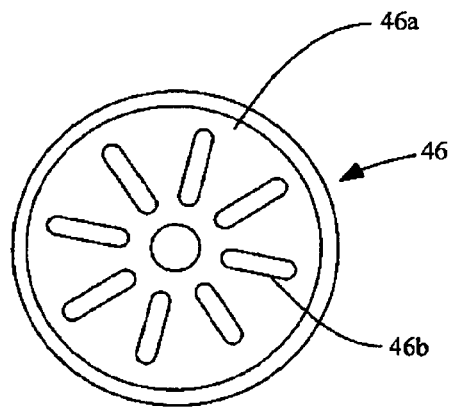
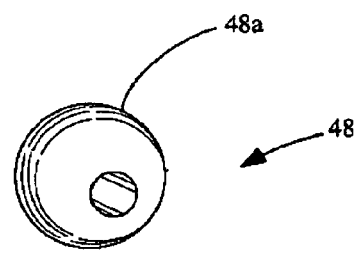
Fig. 28A      Fig. 28B
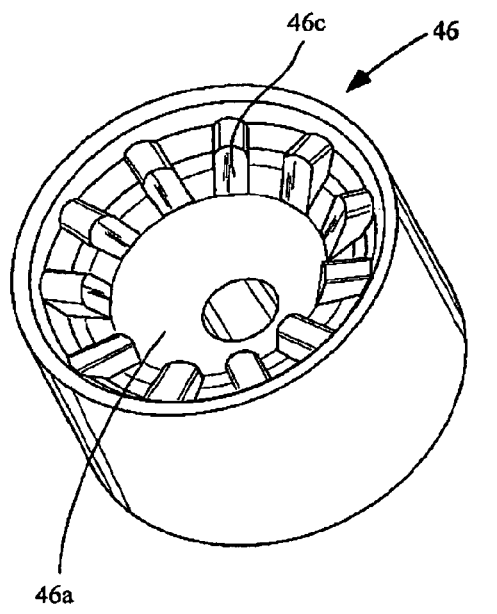
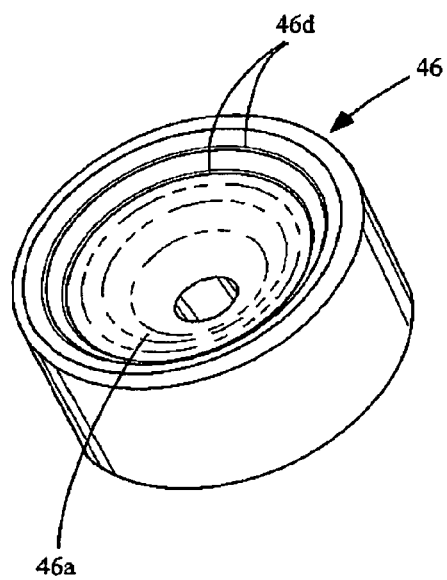
Fig. 28C      Fig. 28D

ORGAN MANIPULATOR APPARATUS

CROSS-REFERENCE

This application is a continuation application of co-pending application Ser. No. 10/615,007, filed Jul. 8, 2003, which is incorporated herein, in its entirety, by reference thereto, and to which application we claim priority under 35 USC §120.

FIELD OF THE INVENTION

The invention pertains to an apparatus for manipulating (and supporting in a retracted position) an organ such as a beating heart, methods of using the apparatus, a system including the apparatus and a stabilizer for stabilizing a select area of the beating heart, and optionally, a sternal retractor. The invention further pertains to method of using the apparatus for manipulating, as well as the systems.

BACKGROUND OF THE INVENTION

Coronary artery bypass grafting (CABG) has traditionally been performed with the use of a cardiopulmonary bypass (CPB) machine to oxygenate and perfuse the body during surgery. Recently, techniques have been developed to allow for performing CABG without the use of CPB by stabilizing the epicardial surface of a beating heart at the coronary anastomotic site with a stabilizer, by contacting the surface of the beating heart with the stabilizer to render a portion of the surface surrounding a target surgical site relatively motionless, to allow placement of sutures through the graft vessel and recipient coronary artery at the target surgical site. This procedure may be performed through a full sternotomy, mini-sternotomy, thoracotomy or mini-thoracotomy, or less invasively through a port provided within the chest cavity of the patient, e.g., between the ribs or in a subxyphoid area, with or without the visual assistance of a thoracoscope.

Access to the left anterior descending (LAD) coronary artery is easily achieved by either a sternotomy or a thoracotomy. However, the patient tropically requires bypass to multiple coronary arteries, including the circumflex artery (CxA) on the left lateral aspect of the heart, the right coronary artery (RCA) on the right lateral aspect of the heart, and the posterior descending artery (PDA) on the back side of the heart. It is very difficult to access the CxA, RCA, and PDA without a sternotomy, as the heart needs to be turned or tilted (or turned and tilted) significantly to reach its side or back, and with an intact sternum, insufficient space exists for these maneuvers. For example, the apex of the heart is generally lifted out of the body through a sternotomy in order to reach the PDA. Surgeons often place the patient in a Trendelenberg position, with the operating table tilted so that the patient's head lies lower than the feet with the patient in supine position, in order to assist with lifting the heart up and back.

An additional challenge to beating heart surgery is that some hearts do not tolerate manipulation well from a hemodynamic standpoint. The potential exists with current manipulation techniques to compress the heart (e.g., by pressing it with stabilization feet) or great vessels in such a way that hemodynamic function is compromised.

There is a need for a beating heart retraction apparatus capable of physically translating a beating heart from its natural resting place to a location better suited to surgical access, and then holding the beating heart in the latter location during surgery without compressing (or otherwise deforming) the heart or great vessels in such a way that hemodynamic function is compromised.

Typically, beating heart surgery has been accomplished through a partial sternotomy using pericardial sutures to retract the heart into the proper position for surgery, and using a stabilization apparatus (e.g., stabilizing feet) to stabilize the portion of the heart surface to be operated on. Sometimes, surgery is performed on the properly positioned heart without using a stabilization apparatus.

However, conventional use of pericardial sutures for retraction of a beating heart has limitations and disadvantages including the following. It is inconvenient and potentially harmful to the patient to incise the pericardium and insert sutures along cut edges of the pericardium, and then exert tension on the sutures to move the heart together as a unit with the pericardium. When the sutures are pulled to lift the heart (with pericardium), compressive force exerted by the pericardium on at least one side of the heart sometimes constrains cardiac contraction and expansion.

There are three distinct stages involved in preparing an artery (on an organ) for anastomosis:

gross manipulation: the organ is physically translated from its natural resting place to a location better suited to surgical access;

artery presentation: the target artery on the organ is identified and the position of the organ is finely adjusted so that the target artery is approachable; and artery stabilization: the target artery and surrounding tissues are immobilized, allowing fine surgical techniques on very small features.

One class of the stabilization devices commonly used to stabilize a target portion of a heart surface (a portion on which surgery is to be performed) are the stabilization devices that comprise rigid ((T-shaped or linear) structures lined with suction cups, such as those described in the article Borst, et al., "Coronary Artery Bypass Grafting Without Cardiopulmonary Bypass and Without Interruption of Native Coronary Flow Using a Novel Anastomosis Site Restraining Device ("Octopus"), J. of the American College of Cardiology, Vol. 27, No. 6, pp. 1356-1364, May 1996, and in U.S. Pat. No. 6,334,843. The stabilization devices described are marketed by Medtronic, Inc. and are known as "Octopus" devices.

It has been proposed to use such an Octopus device to assist in repositioning the heart into a desired position for surgery (by holding the retracted heart in this position), as well as to stabilize a portion of the heart's surface following retraction (gross movement) of the heart. See, for example, U.S. Pat. No. 6,334,843 and PCT International Application WO97/10753 (by Medtronic, Inc.) entitled "Method and Apparatus for Temporarily Immobilizing a Local Area of Tissue," published Mar. 27, 1997, especially with reference to FIG. 33 thereof. However, no conventional Octopus device can support a beating heart with adequate compliance to allow normal heart beating movement, and instead each conventional Octopus device would exert compressive or twisting force on at least one side of the beating heart, thereby constraining cardiac contraction and expansion. Also, one of the small-diameter suction cups of a conventional Octopus device would be too small to reliably grip (and support) the heart without causing trauma to the heart surface. Thus, in order to reliably (but atraumatically) retract and support the heart in the retracted position, many small-diameter suction cups (supported on a rigid frame which frame is itself rigidly supported) need to exert suction simultaneously on the heart, which exacerbates the problem of constrained cardiac contraction and expansion due to the exertion of compressive or twisting force on the heart.

U.S. Pat. No. 5,799,661, which issued Sep. 1, 1998 to Boyd, et al. (and assigned to Heartport, Inc.) describes (with reference to FIGS. 33A-33C) a suction cup manipulator on a long shaft. The suction cup is to be attached to an arrested heart by suction, and the device is then manipulated to move the heart around in the chest cavity. A vacuum is applied to the cup to provide suction, and the vacuum is said preferably to have a value not less than −150 mmHg (to avoid tissue damage). The suction cup is made of "a soft, flexible elastomeric material such as silicone rubber, has a diameter of approximately 12 mm to 50 mm, and has a textured, high friction distal surface (for gripping the heart). The high friction can be achieved by a pattern of bumps or an absorbent high friction material (such as nonwoven polyester fabric). A disadvantage of the bumps is that they would likely cause trauma to the organ being manipulated (even with a vacuum in the preferred range).

U.S. Pat. No. 5,799,661 suggests without explanation that the suction cup is flexibly mounted to the distal end of a rigid shaft, but it is apparent from FIGS. 33A-33B that this simply means that the cup itself has some flexibility so that the cup can bend relative to the rigid shaft. U.S. Pat. No. 5,799,661 does not teach attaching the suction cup to the shaft by a joint which provides limited freedom to translate along a first axis and/or full (or at least limited) freedom to rotate about the first axis, but no significant freedom to translate in directions perpendicular to the first axis. Thus, the suction cup apparatus described in U.S. Pat. No. 5,799,611 is useful only to retract an arrested heart; not a beating heart or other moving organ since the suction cup apparatus of U.S. Pat. No. 5,799,611 does not have compliance to allow for normal organ movement such as a heart beat, and would instead exert compressive or twisting restraint forces on at least one side of the moving organ, thereby constraining cardiac contractility (contraction and expansion) or other normal organ movement.

U.S. Pat. No. 5,782,746, issued Jul. 21, 1998, discloses an annular suction device for immobilizing part of the surface of a heart during surgery. Although the device is said to allow the heart to beat in a "relatively normal" manner during surgery, "the device is rigidly mounted to a fixed mounting structure during surgery, and thus neither the device nor the part of the heart surface which it immobilizes would have freedom to move significantly relative to the mounting structure during surgery. The reference suggests positioning the device on the heart, applying vacuum to the device to cause it to exert suction on the heart, then moving the device to "partially" raise the heart, and then rigidly mounting the device to the fixed mounting structure so that the device supports the "partially raised" heart during surgery.

WO 97/26828 (Gentilli) discloses a laparascopic-endoscopic surgical instrument for grasping and handling parenchymatous and cavum organs. The instrument has a rigid tube with a suction cup provided at the proximal end of the tube. The suction cup is pivotally connect to the end of the tube by a flexible section and stray wires are axially provided along the rigid tube and connected to the suction cup so the orientation of the suction cup can be changed by operating the wires at the distal end of the rigid tube. The rigid tube is connected to a vacuum source at its distal end for application of vacuum to the suction cup. There is no disclosure as to use of the device for manipulating a heart. More importantly, there is no provision for allowing rotation of the organ once it has been grasped by the suction cup, nor is there any provision for even allowing axial movement of the organ once it has been grasped by the suction cup. Only pivoting of the suction cup is provided for and the purpose of such pivoting appears to be for remotely controlling the orientation of the suction cup to align it with the target organ before engaging the organ. Additionally, the flexible member biases the suction cup toward axial alignment with the rigid tube.

SUMMARY OF THE INVENTION

The present invention pertains to improved methods, apparatus and systems for retraction (gross movement) of a beating heart or other organ into a desired position and orientation to allow surgery to be performed on the organ. When the organ has been retracted (in accordance with the invention) into a desired position and orientation, a stabilizer can be used to stabilize a portion of the organ's surface on which surgery is to be performed. However, such tissue stabilization products cannot duplicate the function of the inventive apparatus. Retraction requires lifting and usually rotation of the organ. Devices designed specifically for tissue stabilization are not well suited to those motions.

The apparatus of the invention differs in purpose and form from conventional tissue stabilization devices. The purpose of the inventive apparatus is to move an organ grossly from one position to another and maintain the organ in a desired gross position (without significantly constraining cardiac contraction and expansion or significantly effecting the contractility of the beating heart). The inventive apparatus is not designed to stabilize specific areas of the organ. The shape and nature of the suction member or members of the inventive apparatus differ from the suction cups of conventional tissue stabilization devices in the need to accommodate different anatomy. For example, the inventive suction member can be larger than a suction applicator of a conventional tissue stabilization device. Also, since the inventive apparatus exerts suction over a larger surface area of organ tissue, the required pressure differential can be less than that required by conventional tissue stabilization devices. The low-pressure differential has a clinical benefit in that the potential for creation of hematomas is lessened.

A key difference between the inventive apparatus and both conventional apparatus for tissue stabilization and conventional apparatus for organ retraction is that the inventive apparatus provides system compliance that allows the target organ to maintain substantially normal motion (e.g., normal contraction and expansion in the case that the organ is a beating heart). In the case of a beating heart, this compliance provides distinct clinical value by lessening the negative impact of manipulation on the contractility of the beating heart, and ultimately, the hemodynamics of the cardiac output.

Accordingly, provided herein are organ manipulation apparatus which include at least one suction member configured to exert sufficient force on an organ to move the organ when the suction member is placed against the organ, a relative negative pressure is established in a space between the suction member and the organ, and the suction member is moved. A support structure adapted to be substantially rigidly fixed to a relatively immovable object is provided, and a suspension interconnects the at least one suction member and the support structure, in a ways that allows at least a limited amount of rotation of the at least one suction member with respect to the support member to accommodate natural movements of the organ.

The suspension of an apparatus according to the present invention may further allow a limited amount of translation of the at least one suction member, along an axis of a suction member, with respect to the support structure In several arrangements, a suction member is provided with a substantially rigid shaft or tube extending therefrom, and the suspension includes a roller rotatably mounted in a base member. The roller has an axis of rotation and a bore substantially perpendicular to the axis of rotation, in or through which the substantially rigid shaft is mounted. The base member may be rotatably mounted to the support structure.

At least one variation of the base member includes a biased retention mechanism, with the cooperating support structure having a retention head at an end portion thereof, which is insertable into the base member to form a snap fit with the retention mechanism.

A biasing member may be mounted so as to bias the suction member shaft relative to the roller in a direction of translation. In at least one example, the biasing member is a spring coupled between a stop member on the shaft and the roller.

In other variations, the substantially rigid shaft is fixed with respect to the roller With respect to translation of the substantially rigid shaft relative to the roller, in a direction along a longitudinal axis of the substantially rigid shaft. In these variations, at least a portion of the suspension base member is flexible, thereby allowing limited amounts of translation of the suction member and the roller with respect to the support structure.

The base member may be formed as a clevis, wherein a first end of the roller is inserted in a first arm of the clevis and a second end of the roller is inserted in a second arm of the clevis.

The base member of the suspension may be rotatably mounted to the support structure.

Although the substantially rigid shaft in some embodiments is fixed with respect to translation relative to the roller, it may be rotatably mounted with respect to the roller, allowing the suction member to rotate relative to the roller.

A connector may be fluidly connected to the substantially rigid shaft, which is adapted to connect with a source of vacuum. At least a portion of the connector is rotatable with respect to the substantially rigid shaft.

The suspension may comprise an elastomeric tubular member extending from the suction member which is adapted to be connected with the support structure. The elastomeric tubular member allows a limited amount of translation of the suction member, along an axis of the suction member, with respect to the support structure. First and second stops may be coaxially mounted with respect to the elastomeric tubular member, to define a mounting section therebetween. A hook member adapted to snap fit over the mounting section, interconnects the suction member and the support structure, and allows rotation of the suction member with respect to the hook member.

In another variation, a spring is positioned Within a lumen of the elastomeric tubular member to help prevent kinking.

A flexible tubular member that fluidly connects the suction member with a source of negative pressure may be provided within a substantially rigid tubular member which functions as a support structure or support arm. At least a portion of the flexible tubular member may be pleated.

Another example of a suspension according to the present invention includes a ball having a first passage therethrough and a socket partially constraining the ball but allowing rotation thereof with respect to, the socket, with a substantially rigid tubular member or support arm passing through the first passage. The ball and socket fluidly connects the suction member with the substantially rigid arm via an opening in the substantially rigid tubular member.

The support structure of the manipulation apparatus ma) include an articulating arm have a flexible state and a rigid state. The articulating arm mal include a cable; a plurality of depression disks and balls alternatively threaded over the cable, each of the depression disks having a pair of concave surfaces adapted to engage a pair of the balls; and a tensioning mechanism adapted to apply tension to the cable. The balls and compression disks are compressed against one another upon application of tension to the cable and the articulating arm assumes the rigid state.

The concave surfaces of the depression disks are harder than the balls in several embodiments. The depression disks may included recesses in or protrusions from the concave surfaces.

The depression disks may be formed to have concave surfaces that have a central portion formed of a first material that is softer than a second material which forms an outer portion of the concave surfaces. The first material protrudes slightly from the second material, and the balls are formed of a material that is harder than the first material.

The support structure of the manipulation apparatus may alternatively include a substantially rigid shaft, a substantially rigid, curved arm; or a substantially rigid tubular member.

Various suction members are provided, including a suction member comprising a foam cup having an inside surface and an outside skinned surface. A peripheral of the cup is folded over so that the skinned surface is adapted to contact an organ and form a seal therewith.

Another suction member comprises a silicone cup having an inner lining of open cell foam, wherein the inner lining further comprises a skin at a peripheral thereof.

Yet another suction member includes a cup having internal grooves adapted to apply negative pressure to a surface of an organ even if the organ is sucked inside the cup to contact an inner surface thereof.

A suction member may be provided with a restraint member, that restrains the organ and defines a vacuum baffle chamber between it and the top inner surface of the cup.

Numerous other examples of suction members are described in detail herein, for use in various organ manipulation apparatus as described herein.

An organ manipulation apparatus is described which includes a suction member configured to exert sufficient force on an organ to move the organ when the suction member is placed against the organ, a relative negative pressure is established in a space between the suction member and the organ, and the suction member is moved; a support structure adapted to be inserted through a small opening in a body of a patient; a coupling member into which the support structure is fitted after insertion of the support structure through the small opening; and a flexible suspension interconnecting the suction member and the coupling member. The coupling member may be rotatable with respect to the support structure after coupling the support structure and the coupling member. A binding member math be proved to prevent advancement of the support structure further into the body once the support structure has been positioned as desired.

A surgical method performed on a beating heart is disclosed to include the steps of: applying a suction member of a manipulation device to a surface of the heart; creating suction between the suction member and surface of the heart; moving the suction member to retract the heart into a position that provides access to a surgical site that would be difficult or impossible to access without retraction; connecting the suction member with a compliance mechanism attached to a support arm; and fixing the support arm with respect to a stationary object, wherein the compliance mechanism permits at least limited translation of the heart and suction member with respect to the support arm.

The suction member and heart are rotatable with respect to the support arm, even after fixing the support arm.

The method may further include the steps of contacting a surgical target area on the heart with a stabilizer in the vicinity of the surgical target to stabilize the surgical target; and performing a surgical procedure on the surgical target.

Still further, the stabilizer may be fixed to a stationary object prior to performing a surgical procedure. The contact by the stabilizer may include contacting with a suction stabilizer and applying suction to grasp tissue in the vicinity of the surgical target, and/or applying mechanical pressure to tissue in the vicinity of the surgical target.

Still further, a surgical method performed on a beating heart is described to include the steps of: providing a manipulation device having a suction member, a support arm, and a compliance mechanism interconnecting the suction member and support arm and permitting at least limited translation and rotation of the suction member with respect to the support arm; applying the suction member of the manipulation device to a surface of the heart; creating suction between the suction member and surface of the heart; moving the suction member to retract the heart into a position that provides access to a surgical site that would be difficult or impossible to access without retraction; and fixing the support arm with respect to a stationary object, wherein the compliance mechanism permits at least limited translation and rotation of the heart and suction member with respect to the support arm.

This method may further include the steps of: contacting a surgical target area on the heart with a stabilizer in the vicinity of the surgical target to stabilize the surgical target; and performing a surgical procedure on the surgical target.

Further, the stabilizer may be fixed to a stationary object prior to performing a surgical procedure. The contacting with a stabilizer may be performed with a suction stabilizer or a mechanical stabilizer.

Another disclosed surgical method performed on a beating heart comprises the steps of: providing a manipulation device having a suction member, a support arm, and a suspension interconnecting the suction member and support arm and permitting at least limited movement of the suction member with respect to the support arm; accessing the beating heart of a patient; contacting the suction member of the manipulation device to a surface of the heart; creating suction between the suction member and surface of the heart so that the suction member grasps the surface of the heart; moving the suction member to retract the heart into a position that provides access to a surgical site that would be difficult or impossible to access without retraction; contacting tissue of the heart at or near the surgical site with a stabilizer and stabilizing the surgical site; and performing a surgical procedure at the surgical site.

Further, the method may include the step of fixing the support arm with respect to a stationary object after the step of moving the suction member to retract the heart.

The suspension permits at least limited translation and rotation of the heart and suction member with respect to the support arm.

The method may further include applying suction through a contact member of the stabilizer contacting the heart tissue to perform the stabilization of the surgical site, and the stabilizer may be fixed to a stationary object to maintain the stabilization. Alternatively, a mechanical stabilizer may be applied to accomplish the stabilization.

Still further, a method performed on a beating heart is described to include the steps of: accessing the beating heart of a patient; contacting a suction member of an organ manipulation device to a surface of the heart; creating suction between the suction member and surface of the heart so that the suction member grasps the surface of the heart; moving the suction member to retract the heart into a position that provides access to a surgical site that would be difficult or impossible to access without retraction; contacting tissue of the heart at or near the surgical site with a stabilizer and stabilizing the surgical site; and performing a surgical procedure at the surgical site.

The method may further include the step of fixing or connecting a support arm to the suction member and Fixing the support arm with respect to a stationary object after the step of moving the suction member to retract the heart.

The suspension preferably permits at least limited translation and rotation of the heart and suction member with respect to the support arm.

A system for performing beating heart coronary artery bypass grafting is disclosed to include: an organ manipulation device having a suction member configured to exert sufficient force on the beating heart to move the beating heart when the suction member is placed against a surface of the heart, a relative negative pressure is established in a space between the suction member and the heart, and the suction member is moved; a support structure adapted to be substantially rigidly fixed to a relatively immovable object; and a suspension interconnecting the suction member and the support structure, the suspension allowing at least a limited amount of rotation of the suction member with respect to the support member to accommodate natural movements of the beating heart; a stabilizer device having at least one contact member adapted to contact the surface of the beating heart at or adjacent a location where an anastomosis is to be performed; and a sternal retractor, wherein the support arm and the stabilizer are adapted to be fixed to the sternal retractor.

The suspension of the organ manipulator may further allow a limited amount of translation of the suction member, along an axis of the suction member, with respect to the support structure.

A system for performing beating heart coronary artery bypass grafting is provided to include: an organ manipulation device having a suction member configured to exert sufficient force on the beating heart to move the beating heart when the suction member is placed against a surface of the heart, a relative negative pressure is established in a space between the suction member and the heart, and the suction member is moved; a support structure adapted to be substantially rigidly fixed to a relatively immovable object; and a suspension interconnecting the suction member and the support structure, the suspension allowing at least a limited amount of rotation of the suction member with respect to the support member to accommodate natural movements of the beating heart; and a stabilizer device having at least one contact member adapted to contact the surface of the beating heart at or adjacent a location where an anastomosis is to be performed.

The suspension of the organ manipulator may further allow a limited amount of translation of the suction member, along an axis of the suction member, with respect to the support structure.

These and other objects, advantages, and features of the invention will become apparent to those persons skilled in the art upon reading the details of the apparatus, systems and methods as more fully described below.

BRIEF DESCRIPTION OF THE DRAWINGS

FIG. 9B is a top view of the impermeable material layer of the suction member of FIG. 9A, showing the distribution of through holes through which vacuum is applied.

FIG. 10A is a sectional view of another example of a suction member according to the present invention.

FIG. 10B is a bottom view of the suction member of FIG. 10A.

FIG. 11 is a sectional view of another example of a suction member according to the present invention.

FIG. 12A is a sectional view of another example of a suction member according to the present invention.

FIG. 15A is a top view of a suction member according to the present invention.

FIG. 15B is a side view of the suction member shown in FIG. 15A.

FIG. 15C is an end view of the suction member shown in FIG. 15A.

FIG. 15D is a sectional view of the suction member shove in FIG. 15A, taken along line 15D-15D.

FIG. 17A is a top view of another example of a suspension according to the present invention.

FIG. 17B is a side view of the suspension shown in FIG. 17A attached to a suction member.

FIG. 17C is a perspective view of a roller portion of the suspension shown in FIG. 17A.

FIG. 18A is a top view of another example of a suspension according to the present invention.

FIG. 18B is a view of the suspension shown in FIG. 18A attached to a suction member.

FIG. 19A is a view of a suspension and suction member which are readily detachable from a support arm.

FIG. 19B shows a readily releasable connector for interconnecting a support structure with the suspension and suction member.

FIG. 27A is an exploded view of a portion of an organ manipulation apparatus according to the present invention.

FIG. 27B is an assembled view of the portion shorn in FIG. 27A.

FIG. 27C shows a clevis which forms a portion of the suspension in assembly and which connects the suction member to a support structure.

FIG. 27D shows the portion of FIG. 27B having been attached to and used to position a beating heart, and bringing a support structure into position to relatively fix the positioning.

FIG. 27E shows the support structure of FIG. 27D having been connected with the portion of FIG. 27B.

FIG. 28A shows an example of a depression disk that may be used in the articulating arm shown in FIG. 1.

FIG. 28B shows an example of a ball that may be used in the articulating arm shown in FIG. 1.

FIG. 28C shows another example of a depression disk that may be used in the articulating arm shown in FIG. 1.

FIG. 28D shows another example of a depression disk that may be used in the articulating arm shown in FIG. 1.

DETAILED DESCRIPTION OF PREFERRED EMBODIMENTS

Before the present apparatus and methods are described, it is to be understood that this invention is not limited to particular structures described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a suction member" includes a plurality of such suction members cells and reference to "the vacuum line" includes reference to one or more vacuum lines and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dales which may need to be independently confirmed.

Figure 1A:
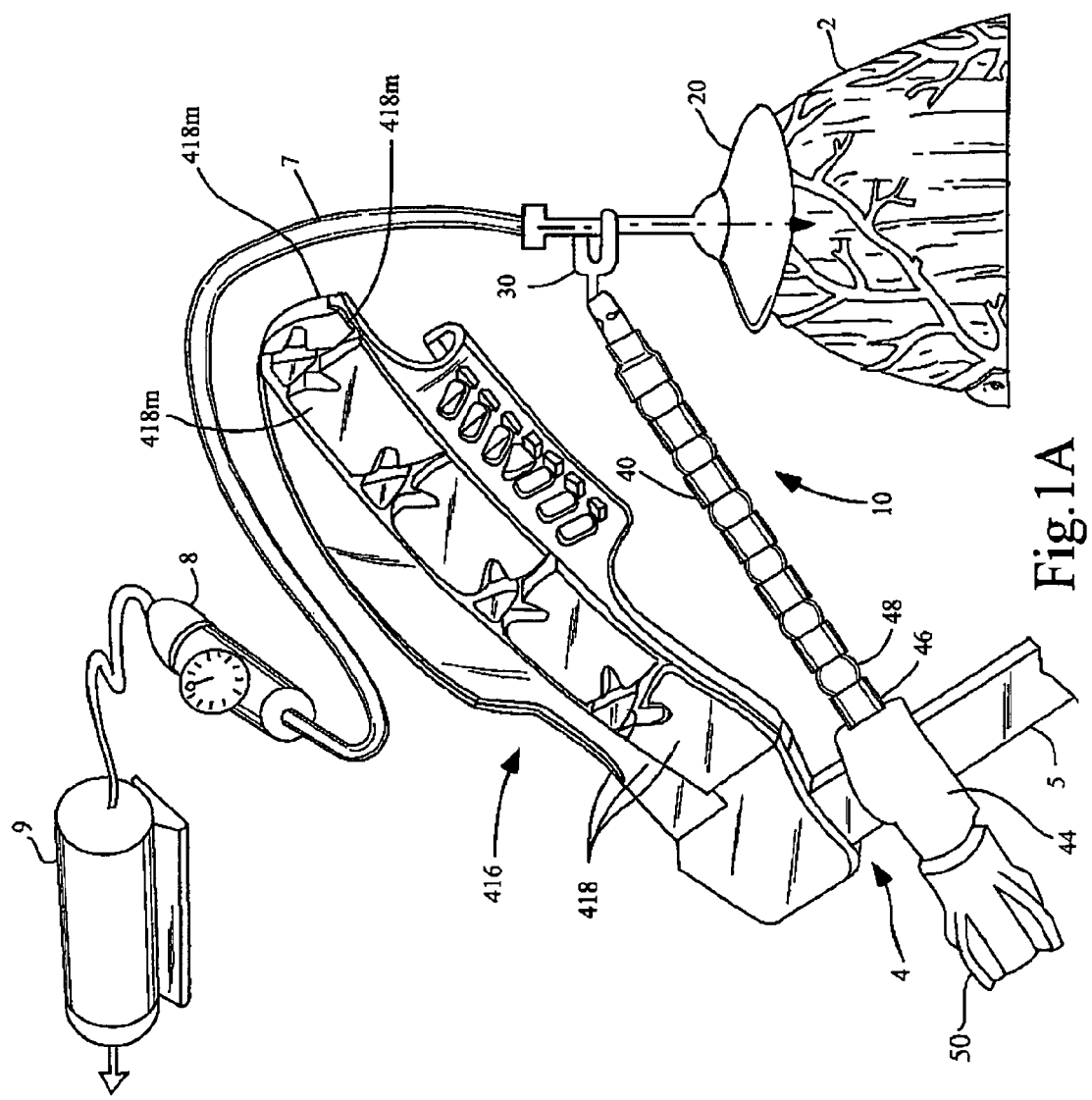
FIG. 1A is a perspective view of an example of an organ manipulation apparatus mounted to a sternal retractor according to the present invention.

Referring to FIG. 1A, a manipulation apparatus 10 is provided to retract heart 2 to a position suitable for performing surgery thereon, and to retain heart 2 grossly in the retracted position, while at the same time allowing limited amounts of freedom to move so as not to adversely effect the pumping action of the heart 2 as it continues to beat. Manipulation apparatus 10 includes a suction member 20 which is adapted to be fluidly connected with a source of vacuum and is further adapted to contact the surface of the heart 2 and engage the heart 2 with application of vacuum thereby attaching to it with an attachment force sufficient to retract the heart as shown in FIG. 1 and to withstand the additional forces applied to it by the beating movements of the heart. Manipulation apparatus 10 further includes a support structure, member or arm 40 which may be rigidly fixed to a stationary member, such as a sternal retractor 4, operating table, ceiling, floor or other relatively immovable object, and a suspension 30 which connects suction member 20 with support arm 40 thereby grossly positioning the suction member while still allowing limited amounts of movement of the suction member with respect to the relatively fixed support arm 40. Thus, suspension 30 performs a very important function in allowing the heart to contract, twist, and otherwise move in a substantially normal fashion, so as not to restrict the contractility and cardiac output of the beating heart while it is in a retracted position.

In this example, a full median sternotomy, has been employed, with the chest cavity being opened at the site of the sternal incision using sternal retractor 4. This approach allows a portion of the heart to actually be lifted up out of the chest cavity for better access to surgical sites, while still allowing the heart to beat relatively normally, as described above. However, the present invention may also be used in procedures using other types of access to the heart, such as a partial sternotomy, sub-xyphoid incision, mini-sternotomy, thoracotomy or mini-thoracotomy, or less invasively through a port or stab wound provided within the chest cavity of the patient, e.g., between the ribs or in a subxyphoid area, with or without the visual assistance of a thoracoscope.

In practice, a retractor, such as retractor 4, for example, (FIGS. 1A and 1D) is inserted into a sternotomy incision such that a pair of opposing blades 414 and 416 each having one or more channels or engaging members 402 adapted to engage opposite sides of an access incision are positioned against the opposite sides of the incision. A drive mechanism, such as a rack and pinion drive mechanism 424 or other well known drive mechanism is used to drive the blades, and thus the sternum apart. In the example shown, rotation of handle 424*a* causes advancement of the pinion over the rack teeth 424*b* of the rack formed on the crossbar 405 of the rack and pinion mechanism 424, thereby driving the opposing blades 414 and 416 apart and causing engaging members 402 to correspondingly force the incision open to provide access to the desired surgical site.

In a sternal approach to the heart, engaging members 402 are adapted to engage each side of the incised sternum to reliably hold and engage the sternum as the sternum is forced open to expose the thoracic cavity and ultimately the heart. Engaging members 402 may be generally in the form of a channel or the like, and have a U-shape, curved shape, or other shape suitable for engaging the incised sternum. Typically, the drive mechanism is constructed to spread the opposing blades apart in a generally parallel fashion, however, the parting motion may also have a significant curvilinear or angular component as well. Also, the retractor may be one which spreads the opposite sides of the rib cage so that they are level with one another in the open configuration, or alternatively, they may be offset, such that one side of the rib cage or opening is higher than the other side in the open configuration.

In addition to engaging members 402, retractor 4 may incorporate a wide variety of additional features which enhance the performance of the retractor system. For example, one or both of blades 14 and 16 may have mounting features to which various instruments used during the procedure can be secured. When an organ manipulation apparatus 10 is to be secured to a stationary object, retractor 4 can serve as one example of a stationary object. It is critical to minimize or substantially eliminate the amount of flex and motion attributable to a support structure, such as support arm 40, to fix the desired location of gross positioning of the heart, from which location, suspension 30 will allow limited amounts of movement of suction member 20 and heart 2 thereabout. When a stabilizer is to be secured to retractor 4 during a beating heart surgical procedure, it is critical to minimize or substantially eliminate the amount of flex and motion attributable to each component and each connection between each component, from the component engaging the beating heart to the component which provides the sternal attachment. To this end, the engaging features 402 which engage the sternum are preferably part of a unitary platform blade structure which also includes mounting features to which an organ manipulation apparatus, stabilizer and other instruments can be mounted. Since the mounting features and the sternal engaging features are part of the same component, and therefore there is no mechanical connection between the two, the stability of an attached instrument against the forces of a beating heart is greatly improved.

In the example shown in FIGS. 1A, 1B, 1D and 29, each of first and second platform blades 414 and 416 include mount features in the form of rails 418. Rails 418 allow one or more instruments to be positioned at any desired location along the operable length of the rail. Additionally, crossbar 5 is dimensioned so that one or more instruments may also be fixed to it, to provide still greater flexibility in positioning instruments in the most desirable locations, from both the perspective of the functioning of each particular instrument, as well as the perspective of maximizing access space and visibility that is available to the surgeon. Preferably, rails 418 are oriented in a direction generally perpendicular to the direction of separation, in this case perpendicular to crossbar 405. The rails may be recessed features within the body of platform blades 414 and 416. More preferably, the mounting rails extend upwardly from the body of platform blades 414 and 416, and extend over at least a portion of the length of the platform blade. Rail 418 may have a top portion and a bottom portion having a narrowed region adjacent the top portion. For example, rail 418 may have a T-shaped cross-section. The T-shaped configuration has a top portion and a narrowed portion, thus forming mounting tabs 418*m* which can be gripped by a number of appropriately constructed mounts. Rail 418 rail may be straight, cured, or a combination of straight and curved portions. Further details regarding the construction and use of a retractor such as that shown in FIG. 28 can be found in U.S. Pat. No. 6,331,158, which is hereby incorporated in its entirety by reference thereto.

When the chest is opened by a median sternotomy as described above, it is possible to gain access to all chambers and surfaces of the heart. The coronary vessels (which are primary target sites in CABG procedures) are surface vessels, only occasionally dipping into the myocardium, making them accessible for CABG without opening the heart. In order to access coronary arteries on the posterior or inferior surfaces of the heart, however, the heart must be lifted, e.g., such as in a manner shown in FIG. 1A. A beating heart CABG procedure requires that the heart be lifted and held in such a way as to minimize any detrimental effects on contractility of the heart, so as to continue substantially normal cardiac output and prevent ischemia, fibrillation and a number of related problems.

Once the heart has been adequately exposed according to the above procedure and is ready to be grossly repositioned, an organ manipulation apparatus 10 is maneuvered to position suction member 20 into contact with a surface of the heart for attachment thereto. With the arrangement shown in FIG. 1A, organ manipulator 10 is preferably fixed to a stationary object such as retractor 4 (e.g. to a rail 418 or to crossbar 5 as shown) prior to contacting suction member 20 to the heart 2 if the situation permits. Alternatively, the suction member 20 may be used to grasp the heart (in a manner described below) prior to fixing the organ manipulator and used to move the heart at least a portion of the distance toward the desired gross positioning location, and then the organ manipulator 10 can be fixed to a stationary object. In either case, the support arm 40 of the organ manipulator 10 shown in FIG. 1A is maintained in a flexible state to allow greater maneuverability during manipulation of the heart 2 and/or attachment of the support arm 40 to the suction member after gross positioning of the heart 2.

In the example of FIG. 1A, suction member 20 is attached to the apex of the heart, which is a region that is commonly used for manipulation of the heart so as help minimize any negative effects on the chamber walls. However, the present invention is not limited to attachment to the apex, as other surface locations of the heart may be grasped by suction member 20 from which vantage point the organ manipulation apparatus is used to reposition the heart. Once suction member 20 has been positioned as desired and contacts the surface of the heart 2, suction is applied to suction member 20 through suction line 7 whereby the suction member grasps the surface of the heart with a force sufficient to move the heart by movement of the suction member, without release, detachment or breaking of the vacuum seal that is formed between suction member 20 and the heart 2. Typically, the suction is applied by a suction accumulator 9 and the amount of vacuum applied is controlled by a suction flow regulator 8.

The organ manipulator 10 is moved so as to pull the heart 2 to a gross position that allows the surgeon access to one or more desired surgical locations. When the heart has substantially reached the desired orientation of the gross positioning, the support arm 40 of organ manipulator is fixed in its present relative position, thereby forming a portion of a relatively stationary support structure for the suction member 20. Thus, support arm 40 remains relatively motionless, while suspension 30 allows limited amounts of movement of suction member 20 (and thus, also the heart 2) relative to the stationary support arm 40, and thereby does not significantly impede the normal beating of the heart or the cardiac output resultant therefrom.

After fixing the gross position of the heart 2 as described above, a tissue stabilizing instrument may be employed to stabilize an area of the beating heart Which includes a target site for a surgical procedure to be performed. For example, a tissue stabilizer may be used for stabilization of a beating heart during a coronary artery bypass graft (CABG) procedure in which the bypass of a narrowed or blocked vessel is performed without application of cardioplegia to the patient and without cardiopulmonary bypass. The tissue stabilizer enables the contacting of the heart and relative stabilization at and in the surrounding area of the portion of the heart contacted to make it possible to perform delicate surgical tasks in that area.

Figure 1B:
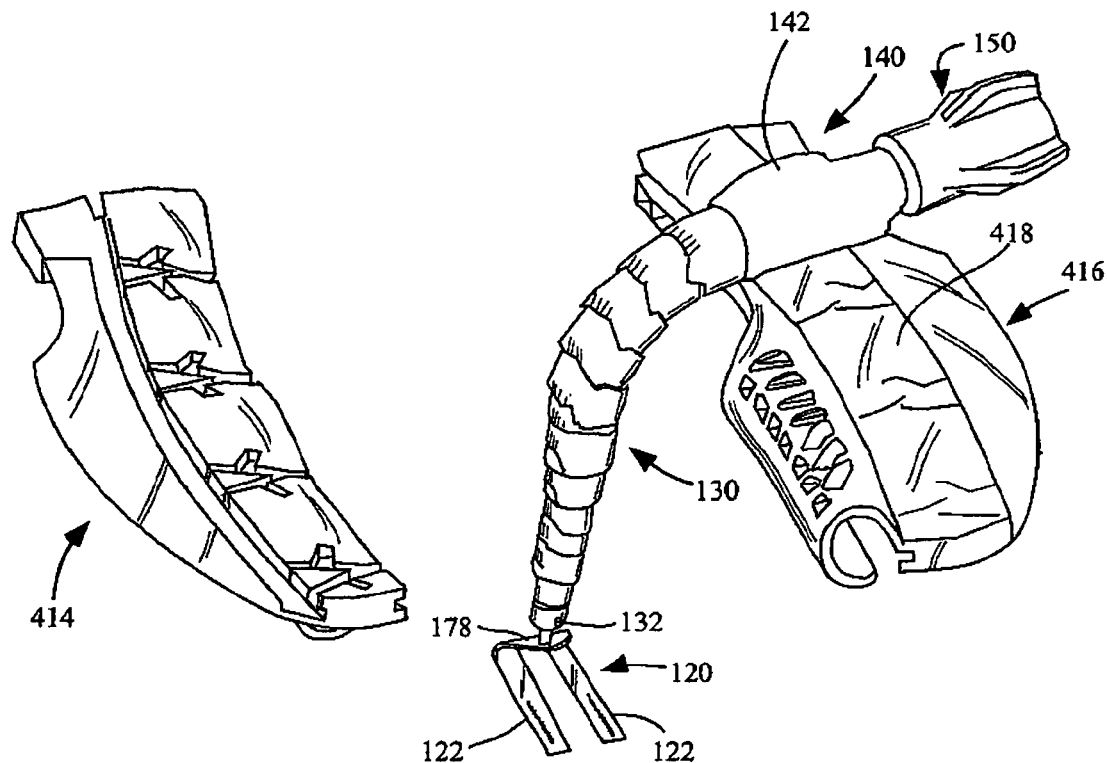
FIG. 1B is a partial perspective view of the retractor of FIG. 1A with a tissue stabilizer mounted thereto to be employed in a procedure with an organ manipulation apparatus according to the present invention.

The tissue stabilizer may, be mounted to a relatively stationary object, (e.g., at a location on one of the rails 418 that provides advantageous positioning of the stabilizer 140, e.g., see FIG. 1B), and is then manipulated so as to bring at least one component of the stabilizer assembly into contact with the beating heart 2 adjacent the target surgical site (e.g., site of the anastomosis). The surgeon typically applies a stabilizing force to the beating heart via the stabilizer assembly, as by applying mechanical pressure through a contact member in contact With the heart tissue in the case of a mechanical stabilizer, or as by applying suction through a suction member in contact with the heart tissue, in the case of a suction stabilizer, until the desired stabilization is attained, and secures the stabilizer assembly in a fixed orientation to maintain the stabilizing force against the beating heart.

The positioning and fixation of the stabilizer assembly substantially eliminates movement of the heart in the target area of surgery to be performed (such as an area in which an anastomosis is to be performed, for example), thereby facilitating the surgeon's placement of sutures and related procedural requirements in performing the anastomosis (or other surgical procedure).

Although, in this example, the organ manipulator 10 and tissue stabilizer are most advantageously employed in combination with sternal retractor 4 used to provide an opening in the chest for direct access to the heart, it would be apparent to one of ordinary skill in the art that one or both of the instruments could be employed separately from a retractor. They are nonetheless adapted to be mounted to a retractor to provide a desirable base of stability. However, other objects of fixation could be utilized if necessary, as known in the art. Further, other types of retractors than a sternal retractor might be employed to achieve access to the heart, and such other retractors (e.g., retractor used in thoracotomy, and other rib separators) could also serve as a base to which the present instruments could be fixed.

Further, the instruments could be advantageously used for their stabilization capabilities in a stopped heart procedure, including procedures employing cardiopulmonary bypass. However, the present instruments are particularly advantageous in beating heart procedures. Although the present instruments may access and stabilize the beating heart in a number of surgical contexts involving various incisions and surgical approaches to the heart as are known in the art, the instruments described herein are most advantageously employed in CABG procedures where the heart is accessed through only one or two minimally invasive incisions in the chest. Particularly, methods involving a sternal retractor are described as well as a method involving intercostal access or access through a stab wound or other small incision.

The anastomosis procedure performed during a CABG operation is a delicate and exacting procedure which requires the installation of very fine sutures (or other connector(s)) around the entire perimeter of the source vessel or graft to attach it to the target vessel in a manner that is substantially leak-proof, for the immediate commencement of delivery of blood to the heart via the surgically altered pathway achieved by the procedure. For this reason, effective stabilization of the anastomosis site is paramount if the surgeon is to effectively perform the suturing/anastomosis task. Also, the working space surrounding the anastomosis site is quite limited, and visibility of the site is also extremely important to the surgeon, who will perform the suturing tasks visually. Thus, instruments involved in the procedure should be minimal in size and place a premium on being located in areas least likely to obstruct the surgeon's view while performing the procedure, while also maintaining sufficient access space for the instruments needed in conducting the suturing and related procedures. The instruments should also be easy to operate and effective at stabilizing a desired area of tissue on the heart. Since this desired area may vary, the instruments should be extremely maneuverable so as to be versatile for use in many, if not all desired target locations on the heart.

A tissue stabilizer employed for this purpose may have one or more stabilizer feet, preferably at least a pair of feet to be positioned on opposite sides of the coronary artery to be operated upon. The contact surfaces of the stabilizer malt be adjustable as to the orientation with respect to the remainder of the stabilizer to adjust to a proper contact of the tissue surface. Various types of stabilizer feet may be employed, including those with one or more mechanical stabilization surfaces, as well as those having one or more contact members that grasp the surface of the heart by suction.

FIG. 1B shows an example of a mechanical stabilizer 140 that may be employed in the present method. Stabilizer 140 is shown mounted on rail 418 of blade 416 of the retractor 4 (note only a portion of the retractor, i.e., blades 414 and 416 are shown in FIG. 1B). The stabilizer 140 is first mounted to the retractor assembly 4 (e.g., at a location on one of the rails 418 that provides advantageous positioning of the stabilizer 140). In the example shown in FIG. 1B, the stabilizer 140 is a multi-jointed device which provides the flexibility needed to reach less direct surfaces of the heart from the incision opening. Additionally, stabilizer 140 is extremely low profile to maximize the amount of free space available in the opening for use by the surgeon. In the example shown in FIG. 1B, stabilizer 140 includes a heart contact member 120 adapted to contact the heart adjacent the site desired to be stabilized. The contact member 120 may include a pair of feet or contact members 122 as shown in FIG. 1B, which may be substantially planar, or slightly curved to conform to the shape of the heart, or one or more may have a non-conforming curve to establish a contact between only a portion of the contact member 120 and the beating heart. The shape of the feet 122 and the contact member 120 may be varied depending on the clinical assessment by the surgeon, the design of the remainder of the stabilizer 140, and/or the design of other instruments to be used to complete the anastomosis.

Figure 1C:
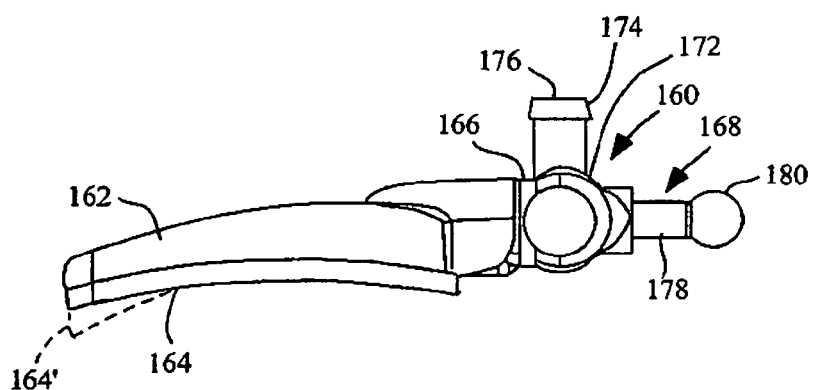
FIG. 1C is a side view of an example of a tissue contact member that employs suction and which may be substituted for the tissue contact member of the stabilizer in FIG. 1B.

As noted earlier, the stabilizer may employ a contact member or members that use vacuum or negative pressure to effect stabilization of the tissue. FIG. 1C shows an example of a contact member 160 that is configured to facilitate the use of negative pressure to engage the surface of the heart. Contact members 162 may each be provided with a thin, compliant seal 164 which is preferably molded into the contact member. Seal 164 is very compliant and flexible, with a Shore hardness of about 50, for example, and tapers similar to a "knife edge", so that it conforms easily to the topology of the tissue that it contacts when a vacuum is drawn through the contact member 162, thereby providing an effective seal between the heart contact member 160 and the tissue. Optionally, the distance that the seal extends from the contact member 602 may scary such that it extends by a relatively greater distance near the tip or distal end of the contact member 162 to provide a variable seal (as shown in phantom by reference numeral 164' in FIG. 1C). The variable seal configuration may help to ensure that a seal is maintained at the distal end of the contact member 162 and that a vacuum pathway is also maintained, as the cross sectional area and thus volume of the distal end is reduced.

Contact members 162 may be connected to manifold base 166. Additionally, the contact members 162 preferably retain the ability to rotate with respect to the manifold 166. Connecting element 168 is fixed to the manifold 166 opposite contact members 162, and which is adapted to connect the contact member 160 to the distal end of stabilizer arm 130. Although various types of connections may be used to perform this task, in the examples shown in FIGS. 1B and 1C, connecting element 168 includes a ball portion 180 that is configured and dimensioned to be received in a socket member contained in distal connector 132 at the distal end of arm 130, and a stem 178 which interconnects ball portion 180 with contact member 160. A rotatable fitting 172 is rotatably connected to manifold 166 and is adapted to fluidly connect the contact members 162 (via manifold 166) with a vacuum line (not shown) that is connected to a source of vacuum. In this way, the contact members 162 and manifold 166 can be rotated while maintaining a constant position of the rotatable joint 172 and the vacuum line connected to it. An inlet lube 174 having an inlet opening 176 is provided to fluidly connect the vacuum line with a hollow space or chamber defined within manifold base 166 and rotatable fitting 172. Further descriptions of the stabilizer contact members described above can be obtained in U.S. application Ser. No. 09/769,964 filed on Jan. 24, 2001, and titled "Surgical Instruments for Stabilizing a Localized Portion of a Beating Heart", which is hereby incorporated by reference thereto, in its entirety.

The present invention is not limited to the use of stabilizers as described above. Any stabilizer that is capable of cooperating with an organ manipulation apparatus according to the present invention to effectively stabilize a portion of the heart in an area of the surgical target, without substantially adversely effecting the continued beating and cardiac output of the heart may be used. Other non-limiting examples and descriptions of stabilizers that may be employed in the present methods include those described in U.S. Pat. Nos. 5,906,607; 5,894,893; 6,036,641; 6,290,644; 6,050,266; 6,213,941; 6,315,717; 6,406,424 and 6,511,416; each of which are hereby incorporated by reference thereto, in their entireties.

Referring again to FIG. 1B, stabilizer 140 includes a highly maneuverable arm 130 which connects the contact member 120 through a base member 142 to a tightening mechanism 150 at the proximal end of the device. The maneuverable arm 130 includes multiple articulating joints which enable the contact member 120 to be positioned and set at a wide variety of positions, virtually enabling the contact member 120 to be used for any target site in performing anastomoses according to the present invention. The multiplicity of articulating joints allow versatile positioning, and a cable which runs through each of the joints and interconnects them with the tightening mechanism 150, may be tensioned to freeze the selected orientation of the device in a rigid configuration. In this way, the contact member 120 can be maintained at the desired orientation to provide stabilization to that portion of the heart tissue with which it makes contact, as well as the immediately surrounding area. A more detailed discussion of the articulating elements, cable, base member and tightening mechanism can be found in U.S. application Ser. No. 09/769,964.

Thus, after mounting the stabilizer 140 to the retractor assembly 4, the maneuverable arm 130 and contact member 120 are manipulated so as to position the contact member against the surface of the heart in the desired area so as to stabilize that portion of the heart to facilitate performance of the anastomosis. When a mechanical contact member is used, a pressure is applied against the heart tissue via contact member 120 which is sufficient to substantially immobilize that area of the heart surface, but not so great as to effect the beating of the remainder of the heart. When a contact member that employs negative pressure is used, a negative pressure is generated between the contact member and the tissue contacted so that the contact member grasps the tissue and stabilizes it. With use of either mechanical contact members or contact members employing negative pressure, when at least a pair of contact members are employed, a further step of spreading the contact members away from one another may be employed to increase the surface tension of the tissue therebetween, which serves to further stabilize the tissue.

Once the contact member or members have been satisfactorily positioned to effectively stabilize an area of tissue, the stabilizer is fixed in position to maintain the stabilization during the procedure to be performed. In the example shown in FIG. 1B, the fixing is accomplished by turning the knob of the tightening mechanism 150 which tensions the cable running through the articulating joints of arm 130 which effectively compresses the joints together, thereby locking them in their relative positions, and at the same time, clamps base member 142 more tightly to rail 418. Of course, various other arms, base members and connectors/joints may be used in a stabilizer to effectively position a contact member and then fix it in that position relative to a stationary object. For example, in place of the articulating arm 130, a rigid arm such as a straight shaft, tubular member or curved arm may be movably mounted to a base member such that it can be repositioned for proper placement of a contact member.

Figure 1D:
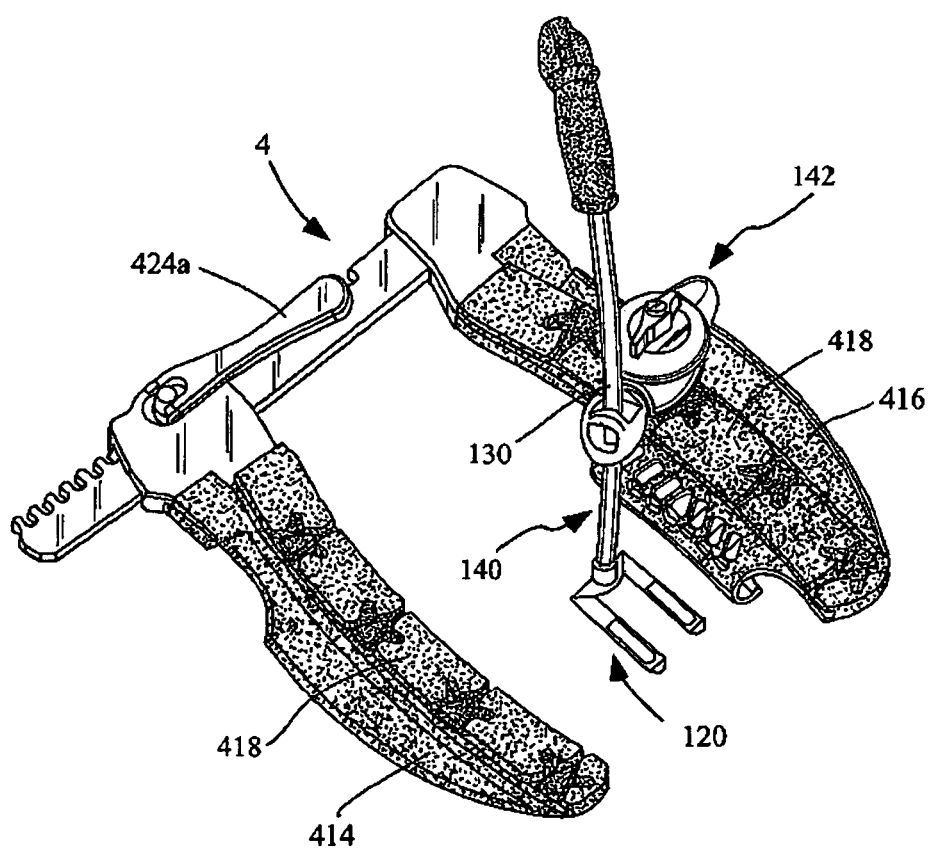
FIG. 1D is a perspective view of the retractor shown in FIG. 1A having a tissue stabilizer mounted thereto.

FIG. 1D shows an example of a stabilizer 140 that is mounted to rail 418 via base member 142. In this example, stabilizer 140 employs a curved, substantially rigid support arm 130, connected to contact member 120 to allow movement of three degrees of freedom of the contact member with respect to arm 130 in an unlocked condition. The base member 142, in this case, includes features to secure base member 142 at a desired position on an appropriately configured mating rail or other suitable structure and includes an arm locking mechanism for controlling and securing an arm of an instrument in a desired position and orientation. One important aspect of this base member 142 is to provide the necessary degrees of freedom to allow the arm 130, and thus the contact member 120 as well, to be easily maneuvered to whatever position may be required by a particular procedure. As discussed above, an additional aspect with respect to stabilizing the beating heart is to eliminate or minimize the flex or motion attributable to the various components and connections of base member 142. Base member 142 is uniquely suited for use in stabilizing the beating heart because it allows sufficient degrees of freedom to easily manipulate the position of an instrument secured thereto, allows the degrees of freedom to be frozen or locked in place and once locked in place, does not significantly flex or allow movement at any of the mechanical joints or connections.

Base member 142 provides a number of different controllable joints that, when in a released condition, allow motion in one or more predetermined directions or about one or more degrees of freedom. Although base member 142 may be used to secure any arm member configuration from straight or curved substantially rigid arms to multi-link or segmented ball and socket type arms which are relatively flexible until themselves locked in some manner at each joint along the arm length, it is most advantageously constructed to provide the joints or connections required to position an instrument having a straight or curved rigid arm 130.

Base member 142 may have three releasable joints or connections for controlling the location and position of the instrument arm 130. The base member 142 may be positioned at a desired location along an appropriate rail and secured by rail grips 144 and 146. The position and orientation of the instrument is then determined by ball joint (or ball and socket joint) 143 between mount base 125 and mount body 126, a rotational joint 147 between mount body 126 and arm hub assembly 127, and an arm clamping mechanism within arm hub assembly 127 which may allow translation, rotation, or both of arm 130 relative to arm hub assembly 127.

Ball joint 143 is preferably of the ball and socket type having 3 rotational degrees of freedom. Rotational joint 147 allows rotation of arm hub assembly 127 about axis 121 as indicated by arrow 113. The arm clamping mechanism allows translation of instrument arm 130 as indicated by arrows 111 as well as rotation about the arm itself as indicated by arrow 117. A further ball-joint type connection 139 may, be employed between arm 130 and the contact member 120 to allow movement of contact member 120 with respect to arm 130 about three degrees of freedom. A locking mechanism controlled by rotatable knob 137 controls the connection 139 between an unlocked state in which the contact member is free to move with respect to arm 130, and a locked state in which the contact member 120 is fixed with respect to arm 120.

Base member 140, having the particular joints and connections identified above, allows all the required areas of the heart to be conveniently and intuitively accessed by a stabilizer connected to one end of a substantially rigid arm. Certainly, base member 140 could be provided with more or less degrees of freedom for maneuvering a particular instrument. For example, to add additional degrees of freedom rotational joint 147 could be replaced with a ball joint and to eliminate degrees of freedom arm 130 could be keyed within arm hub assembly 127 or ball joint 143 could be replaced with a rotation only joint, for example. However, it should be noted that excessive degrees of freedom may tend to make instrument adjustment increasingly difficult and cumbersome to control while too few degrees of freedom may not allow the instrument to be easily placed in the desired position or orientation.

Figure 1E:
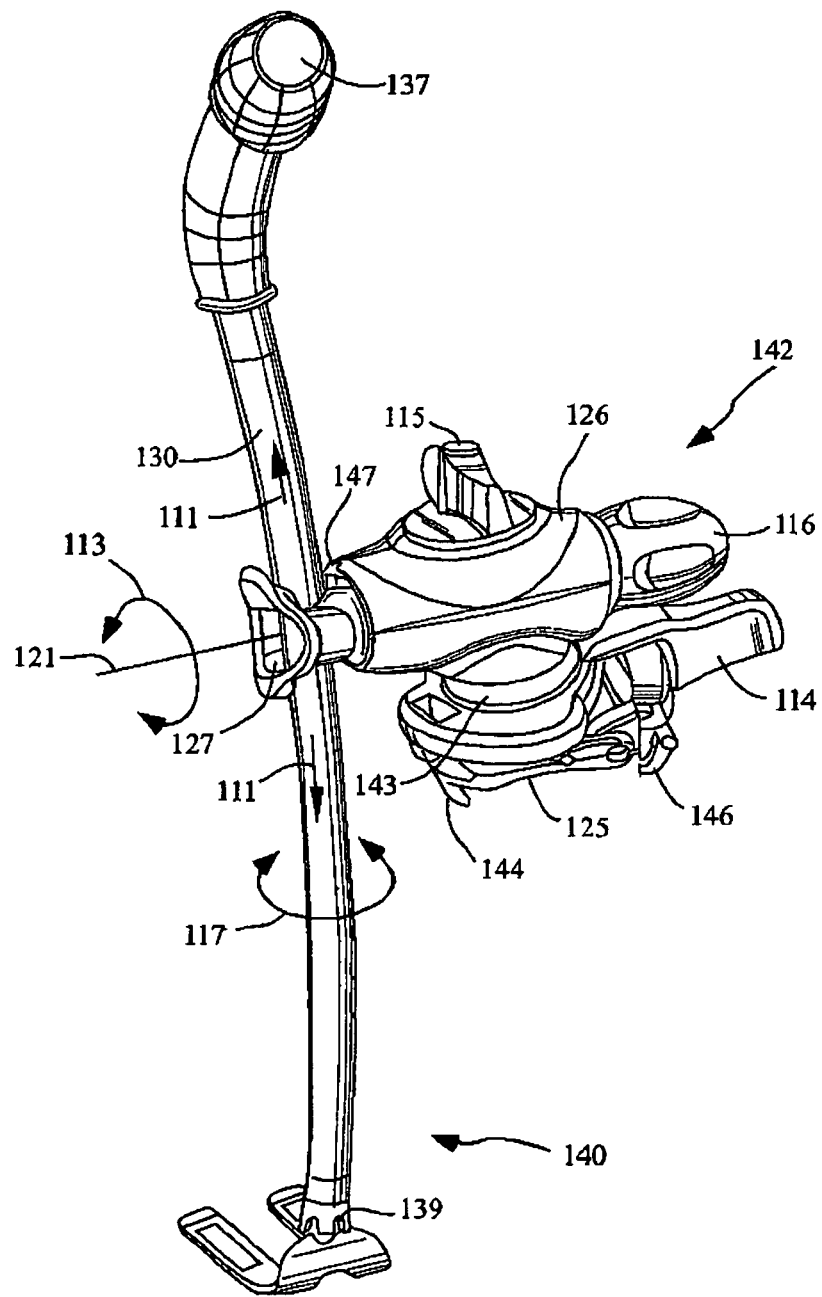
FIG. 1E is an enlarged perspective view of the stabilizer and mounting mechanism shown in FIG. 1D.

In the example shown in FIGS. 1D-1E, the various joints and connections are locked into a desired position by way of a series of knobs. The degrees of freedom provided by ball joint 143 are locked by activation of top mount knob 115. Both rotational joint 147 and the arm clamping mechanism of arm hub assembly 127 are locked in place by the activation of side mount knob 116. Base 125 is locked in position on the rail by activation of mount lever 114. Ball joint 139 may be locked in position by activation of knob 137, as noted above. This particular sequence of knobs used to lock down the degrees of freedom associated with base member 140 tends to allow the user greater precision in positioning the instrument because degrees of freedom unnecessary to a particular desired maneuver of the instrument can be locked down. Most commonly, mount body 126 is placed at a desired angle or orientation and then fixed in place by locking ball joint 143, leaving final adjustment to take place using rotational joint 147 and the arm movement allowed by the arm clamping mechanism of arm hub assembly 127. Again this is just another example of a stabilizer and mount that can be used in conjunction with an organ manipulator according to the present invention to carry out the methods described herein. A more detailed description of the stabilizer and base member mount shoots in FIGS. 1D-1E can be found in U.S. Pat. No. 6,331,158.

Upon completion of the surgical procedure, such as an anastomosis, at the surgical site having been stabilized by stabilizer 140, the contact member 120 is removed from contact with the heart tissue, such as by releasing tension from tensioning knob 150 and manipulating the flexible arm (now in the unlocked, flexible state) and contact member away from the tissue, or by releasing whatever other mechanisms are employed for fixing the stabilizer in the stabilizing position, so as to enable the removal of the contact member from contact with the tissue. In the case of use of a suction stabilizer, the vacuum or negative pressure will, of course, be discontinued prior to removing the contact member from the tissue. After removal of the contact member from contact with the tissue, stabilizer 140 is then completely removed from the site, by removing base member from its location of fixation (e.g., rail 418) and then physically removing the entire instrument.

Repositioning of the heart 2 is performed by unlocking the organ manipulation apparatus 10 from its gross positioning configuration, thereby allowing movement of arm 40 with respect to retractor 4. In the example shown in FIG. 1A, this is accomplished by releasing tension from a cable running through the multiple components of arm 40, by turning tensioning knob 50 in a counterclockwise direction. Suction is maintained between suction member 20 and heart tissue 2 at this time. The now flexible arm is manipulated so as to slowly lower the heart 2 back into is normal position. Upon returning the heart to its normal position, vacuum is discontinued and suction member 20 is removed from its contact with the heart. Base member 42 can then be removed from its location of fixation and the entire organ manipulation apparatus 10 can be physically removed from the site to allow more working space for completing the surgical procedure.

Suction Member

Figure 2A:
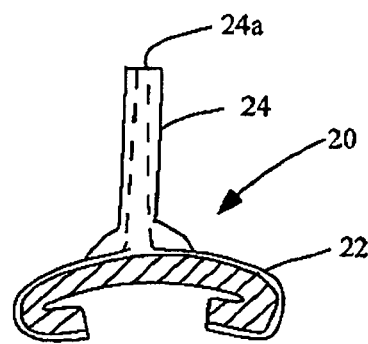
FIG. 2A is a sectional view of one example of a suction member according to the present invention.
Figure 21:
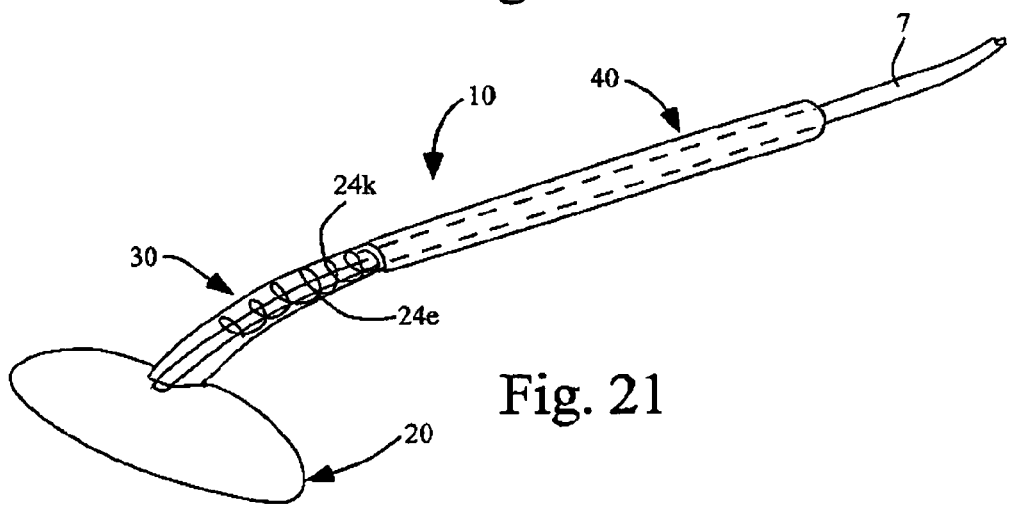
FIG. 21 shows a further example of an organ manipulation apparatus according to the present invention.

Referring now to FIGS. 2A-2E, sectional views of various stages in the manufacture of suction member 20 are shown. FIG. 2A is a sectional view of the completed suction member 20, which, in this case is an all foam contact member 22 having a plastic mounting stem 24 mounted thereto for fluidly connecting the suction member 20 with a vacuum line 7. A rotational connector 38 may be provided to interconnect mounting stem 24 with vacuum line 7 to allow relative rotation between these two components, so that when suction member rotates with the heart, suction line can remain in the same position, thereby preventing tangling or additional forces on the heart that may be detrimental to the normal beating of the heart. Suction member 20 in FIG. 21 is adapted for use on either the apex of the heart of on the ventricles. The foam contact member 22 is more compliant than a silicone cup and provides greater cushioning of the heart tissue, thereby reducing the risk of hematoma or other trauma to the heart tissue caused by grasping it with a suction device.

Figure 2B:
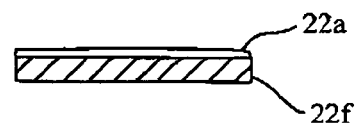
FIGS. 2B-2E are sectional views of various stages of making the suction member of FIG. 2A.
Figure 2C:
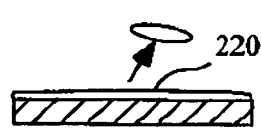
Figure 2D:
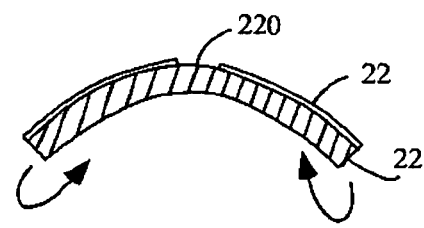

Initially, a foam disk (e.g., polyurethane or other biocompatible foam) is molded to have a skin 22a on one side thereof, as shown in FIG. 2B. The skin 22a is substantially air impermeable, which is necessary in order to generate a pressure differential between the inside and outside of the contact member. The remainder of the body of the foam 22f, of course, is porous and allows air flow; therethrough. A central opening 22o is formed in the skin, such as by cutting or drilling to remove a small disk 22d of the skin, as shown in FIG. 2C. Next, the foam disk is flexed or bent as indicated in FIG. 2D, thereby beginning to form the cup-shape that the contact member 22 will eventually assume.

Figure 2E:
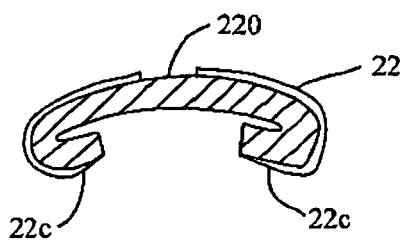

In order to form the necessary airtight seal that is required for forming a vacuum against the tissue surface and thereby grasping it, the contact surface c of the contact member must also be substantially air impermeable. Otherwise, air Would be able to flow or leak through the periphery of the disk is the porous layer 22f contacted the tissue and a vacuum were attempted to be drawn. To make the contact surface impermeable, the edges of the disk are folded under, as shown in FIG. 2E and bonded to the underside of the disk, using either a biologically acceptable glue or heat bonding, for example. Finally, stem or shaft 24 is centered over the central opening 22o and bonded to the skin 22a for complete the configuration shown in FIG. 2A. Upon application of vacuum through the annulus 24a of shaft 24 air is filtered through the multiplicity of pores in the foam member 22 and then drawn through opening 22o and finally into the annulus 24a. Advantageously, the foam 22f diffuses the air flow and prevents tissue from being sucked up into opening 22o or annulus 24a thereby greatly contributing to prevention of suction blockage by the tissue and reduction of trauma to the tissue.

Figure 3:
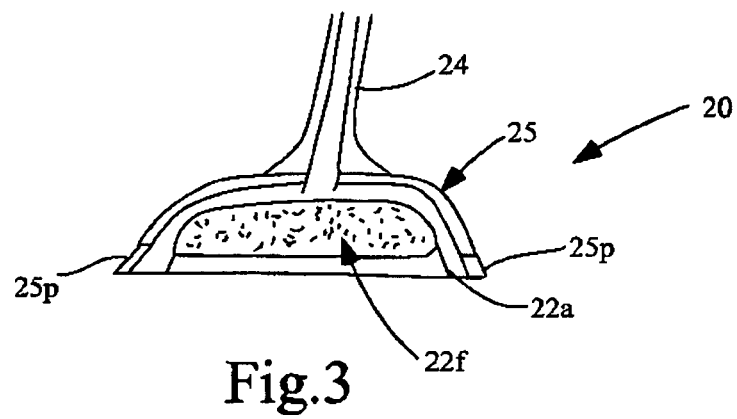
FIG. 3 is a sectional view of another example of a suction member according to the present invention.

FIG. 3 is a sectional view of another example of a suction member 20 according to the present invention. This is similar to that shown in FIG. 2A in that an open-celled foam 22f having an outer skin 22a is provided. However, this suction member further includes an outer shell member 25 made of a material that is stiffer or more rigid that foam 22, a material such as a soft silicone, for example. The silicone layer may extend flush with t4h skin 22*a* at the opening of the suction member, or, alternatively, may not extend that far (as shown by the phantom lines 25*p*) so that the interface between the suction member 20 and tissue is more flexible and forms a better seal that is more resistant to leak-age. The shell member 25 makes it less likely that a vacuum drawn within member 20 can collapse the space in which the vacuum is created, thereby enabling a relative large volume of open-celled foam to diffuse the air flow and cushion the tissue that is drawn into the vacuum space.

Figure 4:
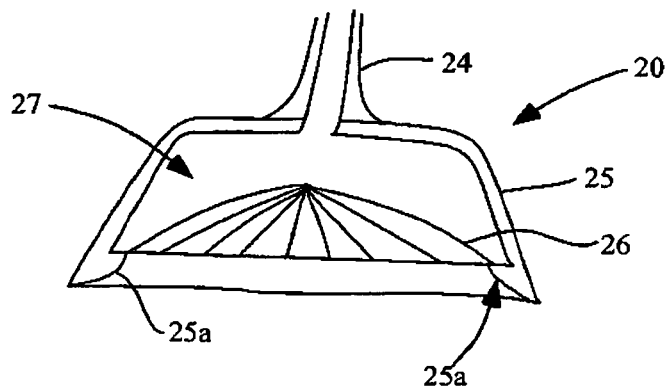
FIG. 4 is a sectional view of an example of a suction member having a tissue restraint member therein.

FIG. 4 shows another variation of a suction member 20 in which a shell member 25, similar to that in FIG. 3 is employed. However, rather than providing an open-celled foam layer interiorly to shell member 25, this variation includes a tissue restraint member 26 (such as webbing which may be formed of nylon strands or the like, for example) which functions to restrain or limit tissue from being drawn any further into the suction member 20. That is, when suction is applied, tissue can be sucked into the suction member until it contacts the tissue restraint member 26, but, since tissue restraint member 26 is substantially inextensible, it substantially prevents migration of tissue beyond the boundary defined by tissue restraint member 26. An additional benefit is that the tissue restraint member 26 prevents the tissue from being overstretched or overstressed by the applied vacuum, thereby preventing bruising, tearing and other trauma to the tissue. A vacuum baffle chamber 27 is defined between tissue restraint member 26 and the inner surface of shell member 25 in which tissue is prevented from entering by tissue restraint member 26 upon application of vacuum through shaft or tube 24. Thus, vacuum baffle chamber ensures that a suction pathway is maintained between the tissue and the annulus of the substantially rigid shaft 24. The shell member is sufficiently rigid to prevent collapse thereof under vacuum, thereby ensuring that the vacuum baffle chamber 27 is maintained. The inner lip 25*a* of the shell member is highly rounded to form an atraumatic surface for grasping the tissue. The tissue restraint member 26 is attached above the highly rounded lip 25*a* by any of the aforementioned attachment techniques.

Figure 5:
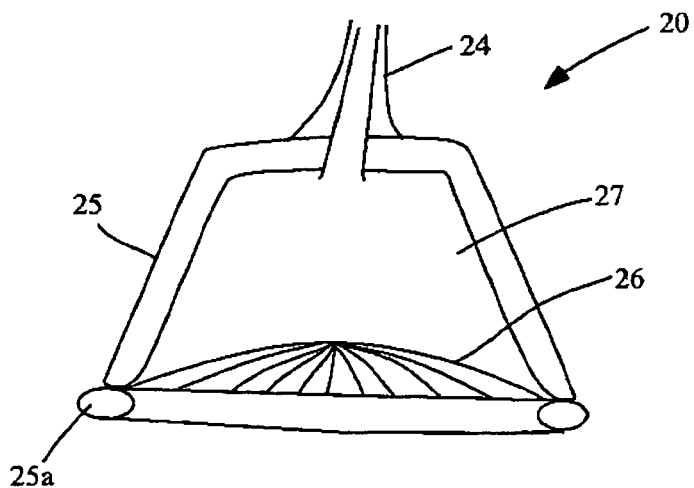
FIG. 5 is a sectional view of another example of a suction member having a tissue restraint member therein.

FIG. 5 is a sectional view of another example of a suction member 20 having a tissue restraint member 26 therein. In this example, a hard plastic cup 25, made of a hard/rigid and biocompatible plastic assures that no deformation of the shell 25 occurs under application of vacuum. Tissue restraint member 26 functions in the same manner as that described with regard to the example in FIG. 4 and is therefore not repeated here. In order to form an adequate vacuum seal with the tissue, the opening of this variation is provided with a foam seal 25*a* around the perimeter thereof Foam seal does deform upon contact with the tissue and formation of a vacuum in the vacuum baffle chamber 27, thereby forming a better, more air impermeable interface with the tissue that it is deformed against.

Figure 6:
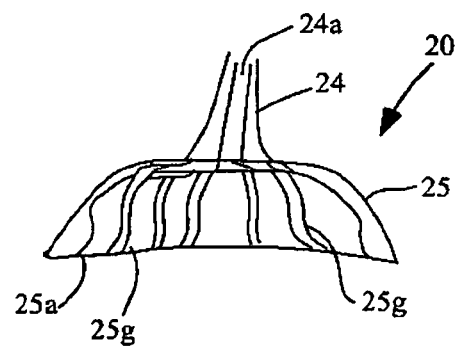
FIG. 6 is a sectional view of a suction member that includes grooves to maintain an open vacuum flow path upon contact of the suction member and application of vacuum to tissue.

FIG. 6 is a sectional view of another variation of a suction member 20 according to the present invention. In this variation, the contact member is formed of a soft elastomeric cup such as a silicone cup 25. Cup 25 that includes grooves 25*g* in the inner wall thereof, each of which fluidly connect with annulus 24*a* of shaft member 24. In this way, upon contacting the suction member 20 with tissue and applying vacuum through annulus 24, even if tissue is sucked up into the suction member so far as to contact the inner walls of the cup 25, grooves 25*g* ensure that an open vacuum flow path is maintained and therefore the suction member does not lose its grasp of the organ it is applied to, since the vacuum is maintained. Even if the tissue presses against the entire inner surface of the cup 25, the channels or grooves 25*g* maintain open pathways for the vacuum. Thus, a very low profile cup can be made with little risk of clogging or blocking of vacuum.

Figure 7A:
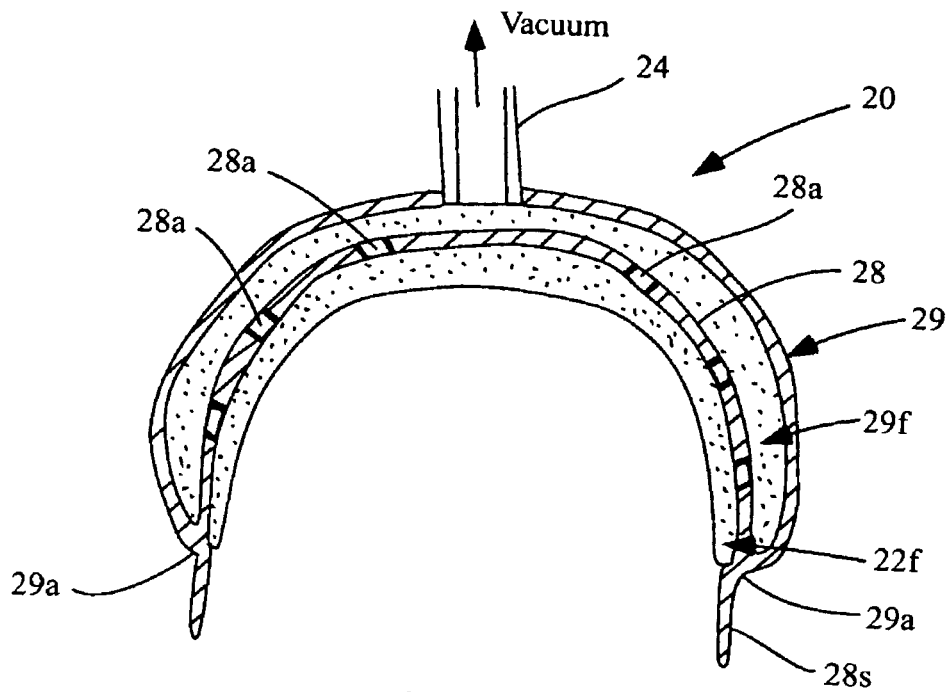
FIG. 7A is an impermeable layer with a hole pattern formed therein.
Figure 7B:
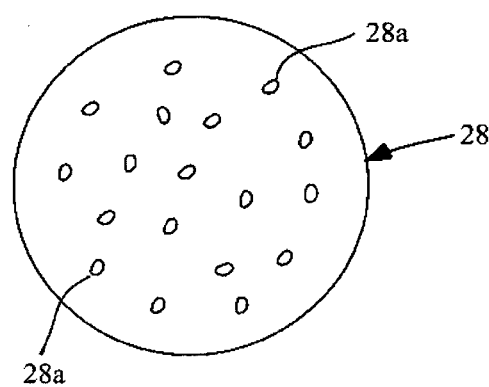
FIG. 7B is a top view of the impermeable layer with a hole pattern formed therein of the suction member of FIG. 6.

FIG. 7A is a sectional view of a suction member 20 that includes an impermeable layer 28 with a pattern of holes 28*a* formed therein to allow air flow therethrough upon application of vacuum through shaft or tube 24. FIG. 7B is a top view of the impermeable layer 28 which more clearly shows the hole pattern formed by holes 28*a*. The hole pattern shown is random, but is not necessarily so. All that is required is a pattern that is disperse over the surface of the impermeable layer 28, as this serves to disperse the flow pathways of the applied vacuum which greatly reduces the chance of completely blocking the vacuum flow paths with tissue. This suction member is configured to be used preferably at the apex of the heart, although it may be applicable to other locations on the heart and is applicable to use on other organs.

An open cell foam layer 22*f* lines the majority of the inner surface of layer 28 and at least covers each hole 28*a*. The open cell foam layer 22*f* further disperses the vacuum flow to provide an even distribution of the vacuum over the surface of the tissue that is contacted by it. Open cell foam layer 22*f* also enhances the structural integrity of the suction member 20 and helps prevent impermeable layer 28 from collapsing or buckling under the applied vacuum load. A thin, flexible skirt extends from the periphery of the impermeable layer 28 and beyond the periphery of open cell foam layer 22*f*, to enhance the sealing function of the suction member at the location of contact with the tissue. Skirt 28*s* may be made of a soft, flexible silicone, for example, and may be an extension of impermeable layer 28, or may be made of a separate softer durometer material than the impermeable layer 28. Impermeable layer 28 is further supported to prevent collapse by outer foam layer 29*f* which covers all or the majority of the outer surface of layer 28 and at least covers each hole 28*a*. The open cell foam layer 29*f* may be made of the same material as layer 22*f* with the same porosity. Alternatively, a different open cell foam may be used, and whether the same material as used or not, the porosity of layer 29*f* may be chosen to be smaller or larger than that of layer 22*f*. Foam layer 29*f* fluidly connects holes 28*a* with the tube or shaft 24 which is to be connected to a vacuum line for supplying negative pressure to the suction member 20. An outer impermeable layer 29 overlays outer foam layer 29*f* and seals with impermeable latter 28 peripherally all the way around the layer 28 at a location 29*a* beneath all holes 28*a*, as well as with the substantially rigid shaft or tube 24, so as to prevent any vacuum leakage between holes 28*a* and the annulus of tube 24. Outer impermeable layer may be a silicone layer or made from some other flexible, substantially air impermeable elastomer or material that is biocompatible. Outer impermeable layer 29, as opposed to layer 28, contains no holes since it performs a containment function, rather that a dispersal function.

Figure 8A:
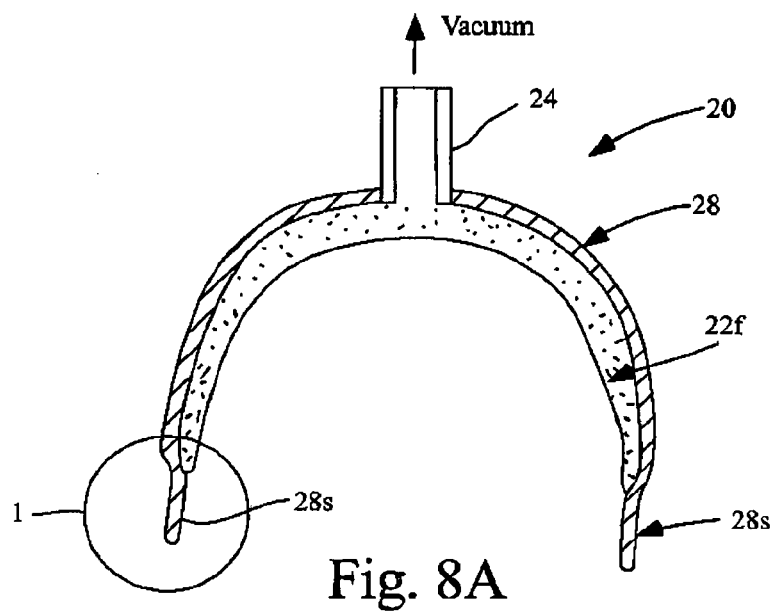
FIG. 8A is a sectional view of a suction member having a thin skirt peripherally located at the opening of the suction member.
Figure 8B:
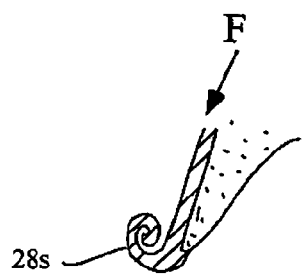
FIG. 8B is an enlarged view of the portion of FIG. 8A defined by circle 1, and showing the deformation that the thin skirt undergoes upon contacting an organ.

FIG. 8A is a sectional view of a suction member 20 that includes a malleable or flexible impermeable layer 28 to establish a vacuum space on the inside thereof when a negative pressure is applied through shaft, tube or stem 24 which is fluidly connected with the space defined by the inner surface of impermeable layer 28. This suction member is configured to be used preferably at the apex of the heart, although it may be applicable to other locations on the heart and is applicable to use on other organs. An open cell foam layer 22*f* lines the majority of the inner surface of layer 28 and provides support and structural integrity to layer 28 to prevent it from buckling or collapsing under the application of vacuum. The open cell foam layer 22f further disperses the vacuum flow to provide an even distribution of the vacuum over the surface of the tissue that is contacted by it. A thin, flexible skirt 28s extends from the periphery of the impermeable layer 28 and beyond the periphery of open cell foam layer 22f, to enhance the sealing function of the suction member at the location of contact with the tissue. Skirt 28s may be made of a soft, flexible silicone, for example, and may be an extension of impermeable layer 28, or may be made of a separate softer durometer material than the impermeable layer 28. Skirt 28s may taper in thickness, as shown in FIG. 8A, so that it is thinnest at the end away from where it connects with layer 28. This further enhances the flexibility and sealing function of the skirt. As demonstrated in FIG. 8B, skirt 28s can be retracted or "rolled up" upon initially placing suction member 20 in contact with tissue to be grasped. Then, upon release of the skirt 28s (which may be retracted manually, for example), the skirt 28s "rolls down" on the tissue to closely conform to the contours of the tissue thereby forming a superior seal. Thus, upon placement of suction member 20 and seal as described, a negative pressure is next applied through tube 24 which draws air existing between the tissue and suction member 20 through dispersed flow paths defined by the porosity of layer 22f and into tube 24. This flow causes a suction force that increases the strength of the air proof seal between skirt 28s and the tissue. The dispersed flow paths through foam 22f tend to distribute the suction force fairly evenly over the surface area of the tissues which is bounded by skirt 28s, thereby reducing the chances of focusing a small portion of tissue with the vacuum flow and pulling it into suction member 20 by an excessive amount which could block the vacuum flow and cause release of the seal and/or damage the tissue.

Figure 9A:
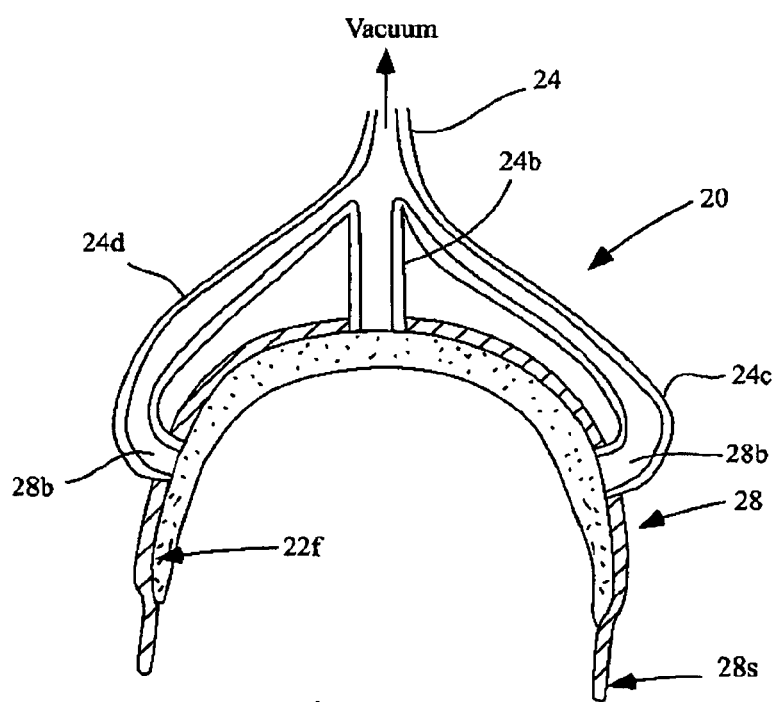
FIG. 9A is a sectional view of another example of a suction member having a thin skirt.

FIG. 9A is a sectional view of another variation of a suction member 20 that includes an impermeable layer 28. In this impermeable layer 28, a plurality of openings 28b are formed, each at a location where a vacuum tube 24b,24c,24d, etc. is joined to fluidly connect with the interior of the suction member. Each of the plurality of vacuum tubes joins into the substantially rigid shaft 24 where they are fluidly connected with a source of vacuum. This suction member is configured to be used preferably at the apex of the heart, although it may be applicable to other locations on the heart and is applicable to use on other organs. An open cell foam layer 22f lines the majority of the inner surface of layer 28 and covers at least each opening 28b. The open cell foam layer 22f further disperses the vacuum flow to provide an even distribution of the vacuum over the surface of the tissue that is contacted by it. Open cell foam layer 22f also enhances the structural integrity of the suction member 20 and helps prevent impermeable layer 28 from collapsing or buckling under the applied vacuum load. A thin, flexible skirt 28s extends from the periphery of the impermeable layer 28 and beyond the periphery of open cell foam layer 22f, to enhance the sealing function of the suction member at the location of contact with the tissue.

FIG. 9B is atop view of the impermeable layer 28 of the suction member 20 shown in FIG. 9A. As shown, impermeable layer 28 includes a regularly spaced pattern of openings 28B (six in this case, although greater or fewer openings could be employed) surrounding a central opening 28B and arranged in a ring for even distribution of vacuum Although the central opening 28B is shown larger than the other openings 28B, it need not be so, as all openings could be formed to be the same size and still achieve the desired distribution of vacuum over the inner surface of the suction member. Thus, upon placement of suction member 20 and skirt 28s as described, a negative pressure is next applied through tube 24 which draws air existing between the tissue and suction member 20 through dispersed flow paths defined each of the openings 28b and associated vacuum tubes. Layer 22f further distributes and disperses the flow pathways through the numerous pores therein, so that the applied vacuum is fairly evenly distributed over the surface area of the tissue which is bounded by skirt 28s, thereby reducing the chances of focusing a small portion of tissue with the vacuum flow and pulling it into suction member 20 by an excessive amount which could block the vacuum flow and cause release of the seal and/or damage the tissue. Still further, in the off chance that a vacuum opening 28b does become blocked by tissue, other openings 28b exist to maintain the applied vacuum force to the tissue and therefore the suction member retains its grasp on the tissue and maintains the organ in its desired retracted position.

FIG. 10A is a sectional view of another variation of a suction member 20 that includes an impermeable layer 28, with a plurality of openings 28b, like in FIG. 9A, each at a location where a vacuum tube 24b,24c,24d, etc. is joined to fluidly connect with the interior of the suction member. Each of the plurality of vacuum tubes may be joined into a substantially rigid shaft 24, as described above with regard to FIG. 9A, where they are fluidly connected with a source of vacuum. Alternatively, any one or more of the vacuum tubes may be formed to be substantially rigid so as to connect the suction member 20 to a suspension thereby. Also, each vacuum line may be individually or independently connected to a source of vacuum. Still further, pairs or other groups of vacuum lines may be joined to a connecting vacuum line for connection to a source of vacuum. In this way, it is possible to connect suction member 20 to more than one vacuum source to provide redundancy, if desired. Foam donuts 22d surround each of the openings 28b on the inside of layer 28, as seen best in the bottom view of FIG. 10B. Donuts 22d ma) be made of an open cell foam of the type described above with regard to open cell foam laver 22f. Donuts 22d provide cushioning for the tissue that is grasped by the suction member 20, while at the same time functioning as spacers, to maintain openings 28b at a distance from contacting the tissue and being plugged. This ensures better distribution of vacuum through the porous donuts 22d. Also, there is less attenuation of the vacuum through the vacuum openings than in previously described embodiments, since no foam covers the openings 22d, which can apply vacuum directly through the donut holes. Although a central opening is not shown in FIG. 10A, a central opening 28d (shown in phantom surrounded by phantom donut 22d in FIG. 10B) may optionally be used in addition to the ring of openings 28d. A further characteristic of this configuration is that the impermeable layer retains a greater amount of malleability because a continuous foam inner layer is not provided.

FIG. 11 is a sectional view of another example of a suction member 20 according to the present invention. This is similar to that shown in FIG. 3 in that an outer shell 25 is provided to contain open-celled foam 22f which may or may not have an outer skin. A very thin, soft sleeve 25s is further provided and is very flexible and capable of telescoping as shown in FIG. 11. However, sleeve 25s is molded in a straight extended configuration so that it maintains a memory for the straight configuration. In practice, suction member is applied to tissue such that sleeve 25s assumes the telescoped position shown in FIG. 11 and a vacuum is applied, thereby establishing a seal between the tissue and sleeve 25s. In the case where the tissue is a portion of a beating heart, sleeve 25s, being biased in the extended "memory" position, is biased to "chase" the heart tissue as it retracts during a contraction phase of the heartbeat, and this provides added assurance of maintaining the seal between sleeve 25s and the heart tissue. Thus, sleeve 25s adds compliance to suction member 20 to ensure better maintenance of a seal between the sleeve and moving tissue.

FIG. 12A is a sectional view of another example of a suction member 20 according to the present invention. This example includes a semi-soft outer shell 25 which may be made of a porous foam having a skin on both sides, or may be a dual layer of silicone or other pliable material filled with porous foam. Internally of the shell 25, a porous foam component 22f is provided to distribute the applied vacuum as well as to cushion the material to be grasped and to enhance the structural integrity of the suction member 20. A capacitance chamber 25c may be provided in shell 25 between an opening 25a on the inner surface of shell 25 and tubular member 24, and fluidly connected between the same, to provide additional capacitance for the applied vacuum. The sealing function of this example is enhanced by providing a verb, soft, pleated or accordioned skirt 25p that has the ability to conform well to the tissue that is seals with upon initial placement, and which further has the ability to chase or follow tissue (such as beating heart tissue) as it moves away from suction member 20. Thus, pleated or accordioned skirt 25p functions as a suspension so as to limit adverse effects of the suction member on the natural motions of the heart as it beats.

Figure 12B:
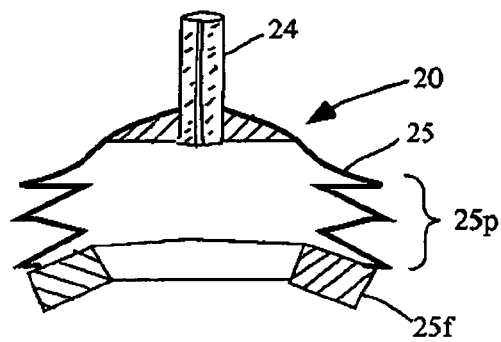
FIG. 12B is a sectional view of another example of a suction member according to the present invention.

FIG. 12B is a sectional view of another example of a suction member 20 according to the present invention, in which a silicone or other equivalent elastomeric material is used to form the main body or cup 25 of the suction member 20, and is constructed with a pleated or accordioned geometry 25p to provide a suspension function and also to provide additional spacing within the body 25 and extensibility to better conform to different geometries along the surface of a heart or other organ or tissue. This configuration enhances the ability to engage on all areas of the heart, and particularly the apex. The deep pocket and suspension like features of the body 25 create a geometry that will readily engage with a curved or flat tissue surface. The suspension further enhances the compliance of the suction member for following the contraction and relaxation of the beating heart. The deep pocket created by the extensibility of this design creates a large volume in which to engage tissue, thereby creating a strong overall hold while at the same time distributing the holding force over a large area so as not to damage the tissue.

A foam diffuser or seal 25f is mounted to the inner flanges at the bottom of body 25 to facilitate the vacuum seal at the location of contact with the tissue to be grasped. The inner flanges further create vacuum pockets that enhance a strong seal upon engagement of the member 20 with tissue. The foam used to form seal 25f is preferably Volara® Zeo (http://www.reillyfoam.com/volara.htm). The seal is die cut from a sheet of the foam material which greatly reduces manufacturing costs.

Figure 12C:
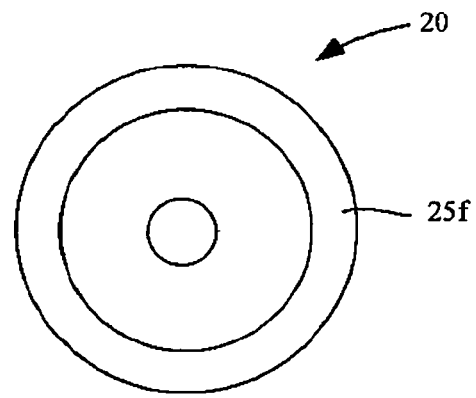
FIG. 12C is a bottom view of the suction member referred to in FIG. 12B.

The body member 25 and corresponding diffuser 25f may be circular in shape as shown in the bottom view of FIG. 12C, they may also be formed in different shapes, such as oval, elliptical or saddle shaped, for example, for conforming to various topographies of tissue surfaces.

Figure 12D:
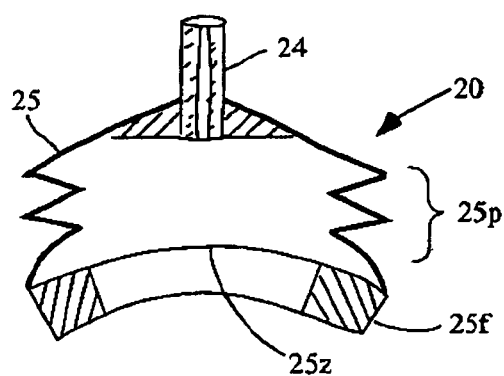
FIG. 12D is a sectional view of another example of a suction member according to the present invention.
Figure 12E:
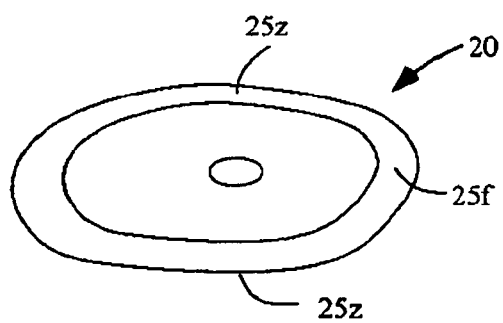
FIG. 12E is a bottom view of the suction member referred to in FIG. 12D.

FIG. 12D is a sectional view of another example of a suction member 20 in which body or cup 25 is made of silicone or other equivalent elastomeric material and is constructed with a pleated or accordioned geometry 25p to provide a suspension function and also to provide additional spacing within the body 25 and extensibility to better conform to different geometries along the surface of a heart or other organ or tissue. This body member 25 and corresponding diffuser 25f are oval-shaped from a bottom view, as shown in FIG. 12E. Additionally, the bottom surface of body 25 is curved upwardly 25z causing conforming diffuser 25f to also have the same upward curvature 25z along the long portions of the oval shape, so as to form a "saddle shape" which conforms well over a curved or rounded tissue surface conformation, such as an apex of a heart for example, thereby enhancing the engagement of the suction member 20 with the tissue.

Figure 13A:
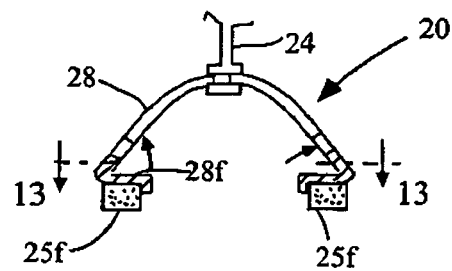
FIG. 13A is a side sectional view of another example a suction member according to the present invention.
Figure 13B:
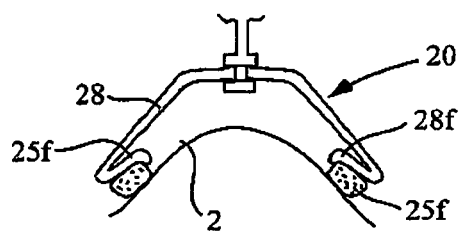
FIG. 13B is a view of the suction member of FIG. 13A in contact with the apical portion of a beating heart.
Figure 13C:
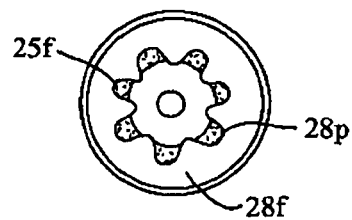
FIG. 13C is a cross-sectional view of the suction member of FIG. 13A, taken along line 13-13.

FIGS. 13A-13C, show another suction member 20 that is deformable to form a seal and enhance organ capture. Suction member 20 preferably comprises elastomeric material 28 (e.g., silicone) having a flat, seal-supporting flange 28f at its distal end. Optionally, a foam seal 25f is attached (preferably by suitable adhesive) to flange 28f. Seal 25f preferably comprises a die-cut, flat, annular piece of foam; flange 28f is also preferably flat and annular. Upon the application of vacuum, the flange member (or flange and foam member) flex into a state in which they conform to the organ's contours as shown in FIG. 13B. In this configuration, seal 25f and/or flange 28f has flexed into a generally frusto-conical configuration. The flexible interface thus provides an excellent seal as it conforms to the contour of tissue adjacent thereto. Further, (though to a lesser extent), it provides the suction member 20 to chase or follow tissue (such as beating heart tissue) as it moves away from the suction member.

FIG. 13C is a cross-sectional view of a preferred implementation of suction member 20 of FIG. 13A when it includes a seal 25f. In this implementation, foam seal 25f is annular, and flange 28f has an inner periphery 29p whose radius varies, e.g., sinusoidally as shown, so as to define cut-outs which expose portions of seal 25f directly to the source of suction. With flange 28f so-shaped, the flange-seal combination may enjoy increased flexibility since the cutouts remove constraints otherwise present on the foam if it were bonded to a full annular flange section.

It is noted that the above-described suction member variations which have been shown and described as being used with a substantially rigid shaft or tube for interconnection with a vacuum tube and vacuum source and a suspension, may be used with other organ manipulation devices described herein. For example, a flexible or elastomeric tubing could be provided for interconnecting any of the described suction members or equivalents with an apparatus of the types described in FIGS. 20 and 21 below. As another example, each suction member could be provided with an opening in a tube or shaft so as to cooperate with the suspension shown in FIG. 24, and so forth. That is, the suction members can be adapted to cooperate with any of the organ manipulation apparatuses/devices described herein.

Suspension

Regardless of the type of suction member that is employed in an organ manipulation device 10 according to the present invention, a suspension 30 is provided which interconnects the suction member with a support structure that is relatively immobile when fixed in a retraction position. Suspension 30 permits limited motion of suction member 20 even after the support structure has been rigidly fixed. This is an important aspect of the organ manipulator, since it permits substantially normal beating of the heart, even as the organ manipulator maintains the heart in a retracted position.

Figures 14A, 14B:
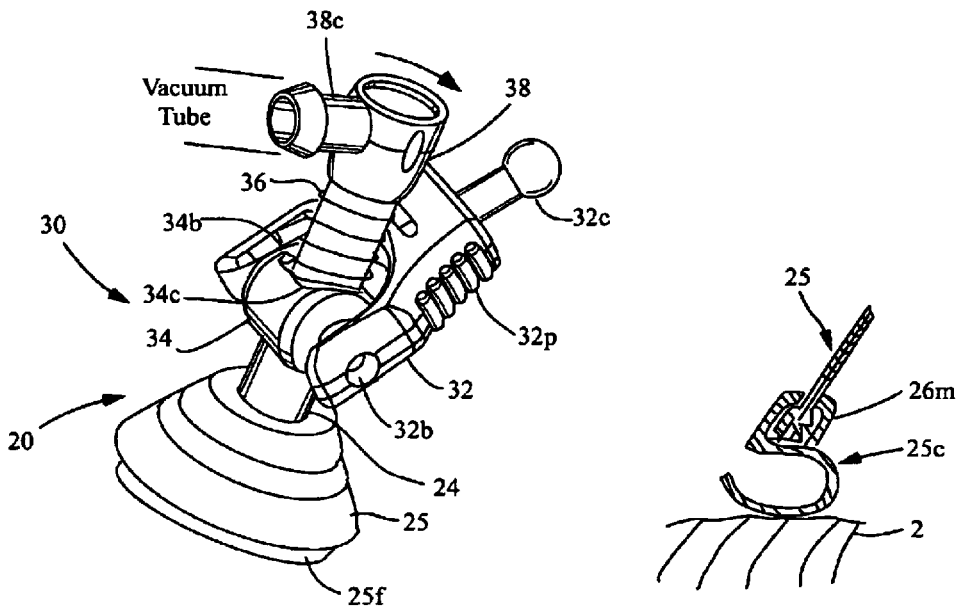
FIG. 14A is a perspective view of a suspension connected to a suction member according to the present invention.
FIG. 14B is a partial sectional view of a suction member having a substantially C-shaped compliant seal.

FIG. 14A shows one example of a suspension 30 which allows both rotation and a limited amount of translation of suction member 20 (and any organ that it may be attached to) with respect to a support structure, such as arm 40, even after arm 40 has been rigidly fixed to a stationary member such as retractor 4. Suspension 30 includes a clevis or fork portion 32 which may be molded from a structurally rigid polymer such as polycarbonate, for example, or machined from stainless steel, etc. Fork 32 includes protrusions 32*p*, knurling or other friction enhancing features that allow the suspension to be more positively grasped and manipulated during both placement of the organ manipulator, and particularly during gross retraction of an organ. A bore 32*b* is provided in each arm of the fork 32 to receive a roller therein. A connector, such as ball and shaft 32*c* extends from clevis 32 and is adapted to rotatably mount suspension 30 with respect to a support arm 40. The shaft portion of connector 32*c* may be press fit into a hole provided in the proximal end of fork 32, for example. Preferably, clevis 30 is rotatable about the longitudinal axis of the shaft of connector 32*c* with respect to the support arm 40 when the support arm has not yet been fixed into a rigid configuration. This allows an additional degree of freedom to rotate the clevis (and suction member 20) for proper orientation of suction member in approximating the tissue to be grasped. After applying suction, grasping the tissue and grossly positioning the organ, support arm 40 is fixed and this also fixes connector 32*c* with respect to the support arm so that fork 32 is no longer rotatable about the longitudinal axis of the shaft of connector 32*c* with respect to support arm 40. Alternatively, the ball of connector 32*c* and distal end of support arm 40 can be configured such that, even after substantially fixing the support arm, the suspension continues to be able to rotate about the longitudinal axis of the stem of connector 32*c* with regard to support arm 40.

Roller 34 may also be molded from polycarbonate and is dimensioned to be received in bores 32*b* to freely rotate within bores 32*b*. In the case where fork 32 is molded from polycarbonate or other substantially rigid polymer, the arms of the fork can be slightly flexed to allow insertion of end pins of the roller 34 into the bores 32*b*. In the case of a metal fork, pins may need to be press fit into roller 34 from outside of bores 32*b* after positioning the main body of roller 34 in place, thereby aligning it with bores 32*b*. Roller 34 further includes a central bore 34*b* dimensioned to receive mounting stem 24 and to allow free rotation and translation of mounting stem 24 with respect to roller 34. Additionally, the rotation of roller 34 about its longitudinal axis allows "swinging" of the suction member about an angular range that is greater than previously described ball joint connectors.

After passing mounting stem 24 through bore 34*b*, a biasing member 36, such as a coil spring for example, is positioned between roller 34 and connector 38. A counter bore 34*c* may be provided in roller 34 that is slightly larger than bore 34*b* and dimensioned to receive an end of biasing member 36, so that it seats in counter bore 34*c*. Connector 38 may be press fit, glued, or otherwise fixed over mounting stem 24 to provide an airtight connection therewith. Connector 38 includes a stem portion 38*c* which is preferably freely rotatable with respect to the portion of connector 38 that is fixed to mounting stem 24, so that when suction member 20 rotates, the suction tube that connects stem portion 38*c* to a source of negative pressure is allowed to remain in substantially the same position, thereby preventing kinking or tangling of the suction tube or line. The outside diameter of connector 38 where it meets biasing member 36 is larger that the outside diameter of biasing member 36. In this way, a limited amount or translation of mounting stem 24 (and thus, also suction member 20 and any organ attached thereto) is allowed, with biasing member 36 tending to bias the shaft in an upward direction and opposing the weight of suction member 20 and an organ attached thereto. The suction member 20 is allowed to freely rotate about 360 degrees with respect to roller 34.

The suction member 20 shown in FIG. 14A is a silicone cup that employs a foam seal 25*f* around the perimeter thereof to facilitate the vacuum seal at the location of contact with the tissue to be grasped. The foam used to form seal 25*f* is preferably Volara® Zeo. The seal is die cut from a sheet of the foam material which greatly reduces manufacturing costs. An alternative seal 25*c* is shown in the partial sectional view of FIG. 14B. Seal 25*c*, although shown as being attached to cup 25, may be used for other configurations of suction members 20 disclosed herein as well. Seal 25*c* is a soft, compliant sealing gasket, which may be made of a soft silicone, for example. Seal 25*c* is molded to have a "C-shape" in cross-section, which compresses when contacted with tissue, as shown in FIG. 14B. Seal 25*c* provides an excellent fluid tight seal with the tissue even under a slight vacuum pressure. The "C" shape of the seal 25*c* enhances its compliance, making it very effective at conforming to the shape of the surface of the tissue with which it makes contact. Although the seal 25*c* is shown to be mechanically interlocked 25*m* with the cup 25, it may additionally, or alternatively be bonded to the cup 25 either with glue, heat bonding, etc. Still further, seal 25*c* may be integrally molded with the cup 25 or other suction member.

FIG. 15A is a top view of another example of a suction member 20 that may be used as an alternate to the suction member 20 shown in FIG. 14A. In this arrangement, the suction body or cup is generally elliptical in shape as shown in FIG. 15A. Like the suction member 20 shown in FIG. 14A, the suction body or cup 25 in this embodiment may be made of a silicone or other equivalent elastomer and has a foam seal or diffuser 25*f* around the perimeter thereof to facilitate the vacuum seal at the location of contact with the tissue to be grasped.

The body 25 and diffuser 25*f* have compound curvature so as to form a saddle-shaped tissue contacting surface. As shown in the side view of FIG. 15B and the sectional view of FIG. 15D, the side portions of the bottom of body 25 and of diffuser 25F curve upwardly, while the end portions of the bottom of body 25 and of diffuser 25F curve downwardly 25*y* as shown in the end view of FIG. 15C. Both end and side walls of the body 25 flare outwardly 25*w* moving from top to bottom so as to form a somewhat bell-shaped body 25. This configuration aids in increasing the depth and volume of the internal vacuum space or pocket 25*e* formed by the walls of the body 25, while maintaining a smaller profile at the top of the suction member 20 as well as focusing the vacuum flow to the center of the top of the body 25. This compound geometry improves the ability of the suction member to engage all areas of the heart, including the apex. The deep pocket 25*e* creates a large volume to engage tissue, which creates a strong engagement or hold on the tissue, while distributing the holding forces over a substantial area of the tissue so as not to damage it.

Figures 16A, 16B:
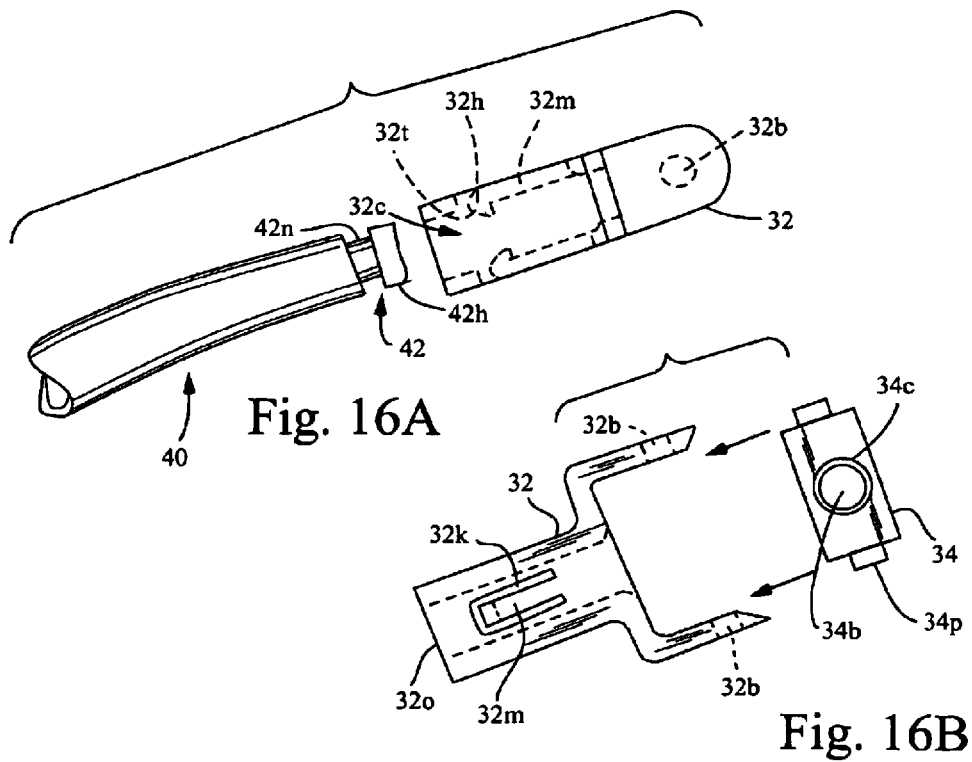
FIG. 16A is an exploded view of a support arm (partial) and a suspension.
FIG. 16B is an exploded view of the suspension shoved in FIG. 16A.

FIG. 16A shows an alternative connector for connecting a support arm 40 with a suspension 30 that is both inexpensive to manufacture and easy to assembly, providing a snap fit between the components. In this example, a rigid, curved support arm 40 is shown, although the connector is applicable to other support arms disclosed herein, such as a straight shaft, a tubular member, a flexible, multiply jointed arm etc. Clevis 32 has a female connector 32*c* as opposed to the male connector shown in FIG. 14A. An opening 32*o* dimensioned to freely allow the insertion of the distal end connector 32*c* is provided in the proximal end of clevis 32. A retention mechanism mart be integrally molded in clevis 32 to include at least a pair of opposing retention members 32*m* which have inwardly extending retention hooks 32*h* that approximate one another so that they are separated by a distance that is less than the diameter "d" of retention head 42*h* provided included as a portion of connector 42. Retention hooks 42*h* are beveled or tapered 427 so that when connector 42 is inserted, retention head 42h abuts the tapered surfaces 42t and the tapered surfaces provide a mechanical advantage for the retention bead 42h to drive the retention hooks 32h apart. Retention members 32m are dimensioned to have a length, thickness and width that gives them a spring constant that is sufficient to bias the retention members toward the positions shown in FIG. 16A.

FIG. 16B shows the tabbed appearance of a retention member 32m separated from the main body of clevis 32 by a channel 32k, except for the distal end of the retention member 32m which is integral with the clevis body 32. In this arrangement, clevis 32 and retention members 32m are integrally molded from a polymer that has good spring characteristics, such as polycarbonate for example. Roller 34 will snap fit into clevis 32, by slightly flexing the fork arms of the clevis and inserting pivot pins 34p into bores 32b.

The neck portion 42n of connector 42 has a diameter or outside dimension which is less than that of head 42h, and preferably, but not necessarily, about the same as the distance between hooks 32h prior to insertion of the connector 42. In this way, after head 42h passes hooks 32h, the biasing force of the retention members 32m forces the hooks inwardly until contacting the surfaces of neck portion 42n. Retention hooks 42h are not beveled on the distal sides of the hooks and therefore lock against the head 42h. Suspension 30 is thereby rotatably connected to support arm 40, retaining the ability to rotate about the longitudinal axis of the clevis 32 with respect to support arm 40, while being prevented from detaching from the support arm by hooks 32m.

FIG. 17A is a top view of another embodiment of a suspension 30 which eliminates the need for biasing member 36. Clevis 32 is formed from a material having elastic properties (such as polycarbonate, for example) and is formed to have a relatively rigid or inflexible portion 32l and a relatively flexible portion 32f, which is substantially along the arms of the fork or clevis 32. Thus, the arms are molded or otherwise formed to have a thickness that, given a fixed length and width, determine an appropriate flexural strength and elasticity of the flexible portion 32f, which functions to allow a limited amount of translation of suction member with respect to support arm 40 when support arm 40 is rigidly fixed to a stationary object.

Mounting stem 24 is press fit into roller 34, so as to maintain a fixed, relative translational position with respect to roller 34, as shown in FIG. 17B. In order to allow mounting stem 24 to rotate with respect to roller 34 however, a bearing 34d (FIG. 17C) is preferably press fit or otherwise fixed with respect to bore 34b. In this arrangement, mounting stem is fixed with respect to the inside surface of the bearing 34d upon press fitting, and rotation of the bearing allows relative rotation between mounting stem 24 and roller 34. When connected to a support arm by connector 32c, and when an organ is grossly positioned in a retracted position by ensuring that support arm is fixed relative to a stationary object, suspension 30 allows suction member 20 to freely rotate by way of bearing 34d, as well as to swing by way of rotation of roller 34 with respect to clevis 32. Additionally, the flexible portion 32f of clevis 32 flexes to allow movement of the organ and suction member in a substantially translational direction along the longitudinal axis of mounting stem 24 with respect to support arm 40.

A variation of the suspension 30 shown in FIGS. 17A-17B is shown in FIGS. 18A-18B. In this example, the flexible portion 32f of clevis 32 is formed from a pair of flexible wires that extend from the inflexible base portion 32i. Wires 32f may be formed from stainless steel or other biocompatible metal exhibiting a sufficient spring constant to suspend the weight of suction member 20 attached to an organ, while further allowing limited translation of the suction member and organ with respect to support arm 40. Wires 32f are preferably molded into inflexible portion 32i for ease of manufacture, but could be attached by gluing or mechanical affixation (screws, bolts or the like). The distal end portions of wires 32f are formed into loops to define holes 32b into which pivot pins 34p are inserted for mounting roller 34. The spring like qualities of wires 32f allow them to be flexed apart slightly to permit insertion of pins 34p into holes 32. After insertion, wires 32f are released and they elastically return to their original positions, thereby capturing the pivot pins whereby roller 34 becomes mounted to clevis 32 while retaining the ability to rotate about its longitudinal axis with respect to clevis 32.

The suspension 30 in FIGS. 19A and 19B operates somewhat differently from the previous two variations just described. In this example, a hook 39 interconnects a support arm 40 with a shaft 24' that is fluidly connected to a vacuum line as well as suction member 20. The opening or aperture 39a of hook 39 defines a gap that is slightly shorter than the outside diameter of shaft 24'. The inside circumference of the hook, or circumference of the space 39b defined inside the hook 39 is slightly greater than the circumference of shaft 24'. Connector 32c preferably becomes fixed with respect to support arm 40 at least when support arm 40 is rigid with respect to a stationary object.

To connect hook 39 with shaft 24', shaft 24' is contacted against the aperture 39a and pressure is applied to slight spread the hook 39 open, thereby enlarging aperture 39a sufficiently to let shaft 24' pass into the opening 39b. Once the shaft 24' is centered in opening 39b, hook 39 elastically returns to its resting configuration where aperture 39a is slightly smaller than the diameter of shaft 24'. In this way, shaft 24' is captured within opening 39b, but not so tightly as to prevent free rotation of shaft 24' within opening 39b. Connector 38 has a diameter greater than the inner circumference 39b of hook 39 and thus acts as an upper stop to prevent hook 39 from sliding upward with respect to shaft 24'. Additionally, a lower stop 24s which also has a diameter or outer dimension greater than the inner circumference 39b of hook 39 is provided to act as a lower stop to prevent hook 39 from sliding downward with respect to shaft 24'. The gap defined between upper and lower stops 38 and 24s may be slightly greater than the thickness of hook 39 to facilitate easier connection of the components. However, the gap should not be so large as to allow an inordinate amount of "free play" in the connection. The connection tube 24e extending from lower stop 24s and fluidly connecting the distal portion of the suction member to shaft 24' is preferably formed of a soft silicone or other highly elastic material. When assembled, the suspension in this example allows rotation of the suction member 20 with respect to the support arm 40 by the free rotation of the shaft 24' that is allowed with respect to hook 39. Elastic tube 24e allows limited amounts of translation of the suction member and organ with respect to the support arm 40, as well as allowing swinging motions of the type that roller 34 allows as well as the type that would be allowed by rotation of connector 32c in previous embodiments with respect to support arm 40.

An additional advantageous feature provided by suspensions 30 of the type demonstrated in FIGS. 19A and 19B is the ability to attach suction member 20 to an organ prior to connecting hook 39 to shaft 24'. This allows more working space for retracting the organ, which may also be grossly positioned prior to connecting hook 39. Thus, suction member can be positioned as desired on an organ to be retracted, and then suction can be applied to fix the position of suction member on the tissue surface of the organ to be retracted. Next the organ can be grossly positioned in a retracted position by manipulating suction member 20 to pull the organ to the desired gross position. Once grossly positioned, hook 39 is attached to shaft 24' as described above, and support arm 40 is fixed in position, so as to maintain the organ in the desired gross position without further manual assistance.

Figure 20:
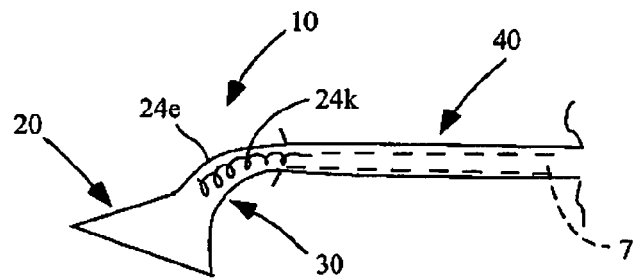
FIG. 20 shows another example of an organ manipulation apparatus according to the present invention.

The organ manipulator shown in FIG. 20 conceals vacuum line 7 within support arm 40, which is, in this example, a substantially rigid tubular member, made of aluminum or stainless steel, or rigid polymer, for example, which may be straight or curved. A multi-link support arm may also be configured in the manner shown in FIG. 20. A curved tubular member 40 provided additional maneuverability of the device. However, a straight tubular member 40 may also be used in intercostal and possibly endoscopic deliveries, depending upon the size and configuration of the suction member 20. The suspension 30 in this arrangement is compact, which is especially important for intercostal and endoscopic deliveries, and includes a thin, highly elastic tubing 24e. The thickness of tubing 24e can be varied to design a suspension having the appropriate spring rate for the mass of the organ to be retracted. The cup portion of suction member 20, tubing 24e and tubing 7 may all be integrally molded in this embodiment. A spring 24k is preferably threaded within the lumen of tubing 24e to prevent kinking of the tubing 24e during bending. With this arrangement, only a limited amount of rotation of suction member with respect to support arm 40 is allowed by suspension 30.

FIG. 21 shows a variation of the organ manipulator 10 of FIG. 20. In FIG. 21, spring 24k is mounted externally over tubing 24e and again functions to prevent kinking of tubing 24e during bending. This arrangement facilitates the use of a smaller diameter tubing 24e that may lessen the resistance to rotation of the suction member with regard to support arm 40. However, the external spring 24k may be slightly more of an obstruction for use intercostally or endoscopically. Once again, however, vacuum line 7 has been integrated within support arm 40 thereby significantly reducing the profile of the organ manipulation device 10 and allowing the surgeon adding working space and visualization of the surgical site.

Figure 22:
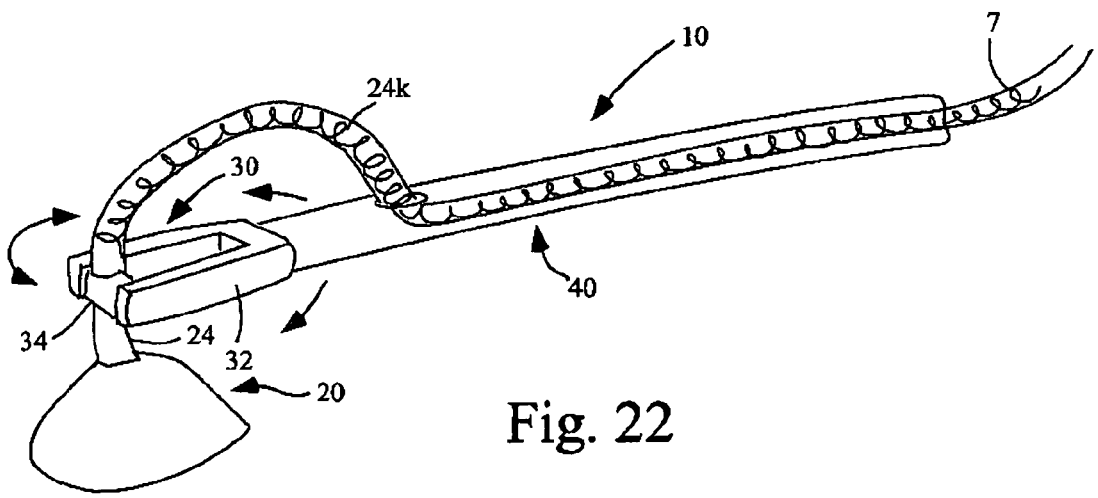
FIG. 22 shows still a further example of an organ manipulation apparatus according to the present invention.

The organ manipulator shown in FIG. 22 combines the vacuum tubing integration function with a suspension 30 of the type described in FIGS. 17A-17B. In this arrangement, a loop of tubing 7 is provided between its connection to shaft 24 and where it enters support arm 40 so as not to provide additional resistance to translatory movements of the suction member 20 with respect to support arm 40. A slot, opening or hole 40a is provided in support arm 40 through which tubing 7 enters. Tubing 7 exits support arm 40 at the proximal end thereof. Preferably, a spring 24k is provided inside tubing 7 along at least the loop portion thereof and preferably along the full length of the organ manipulator, to prevent kinking. Clevis 32 is rotatably mounted to support arm 40 to allow rotation of clevis 32 about the longitudinal axis of support arm 40 with respect to support arm 40. Roller 34 allows swinging of suction member 20 with respect to support arm 40 and the arms of clevis 32 are flexible to allow translation of suction member 20 with respect to support arm 40.

Figure 23:
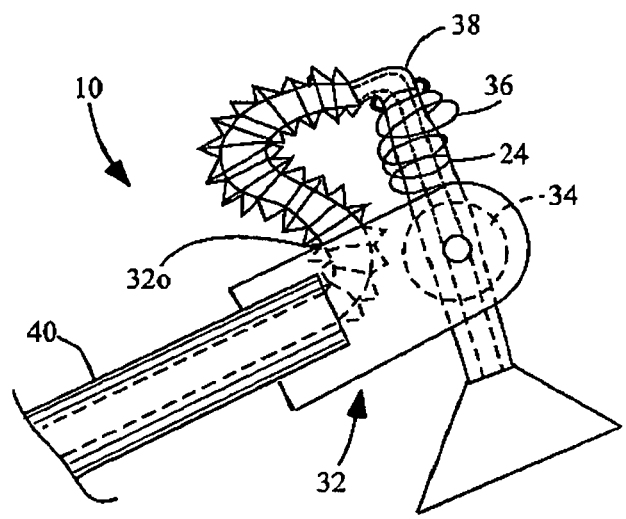
FIG. 23 is a partial view of an organ manipulation apparatus using an anti-kinking vacuum line.

FIG. 23 shows an additional arrangement for integrating vacuum tubing 7 even more completely within the organ manipulation device in which tubing 7 exits through an opening 32o in clevis 32. Support arm may be joined to clevis 32 as described with regard to FIG. 16A or alternatively may be glued or bonded thereto, although this option would eliminate the freedom of the clevis to rotate with respect to support arm 40. Tubing 7 passes through the proximal end of support arm 40 as described and shown previously (not shown in FIG. 23), passes through the distal end of support arm into clevis 32 and out of opening 32o. Tubing 7 connects at its distal end to connector 38. The portion of tubing 7 that is external to the device is pleated or accordioned to allow it to assume the S-shape as shown in FIG. 23 without kinking, cracking or other problems. Additionally, the pleated tubing moves with the shaft 24 more reliably without any of the aforementioned problems, and with less resistance to free movements of the shaft 24 than a standard tubing, which is less flexible and therefore more resistant to such movements.

Figure 24:
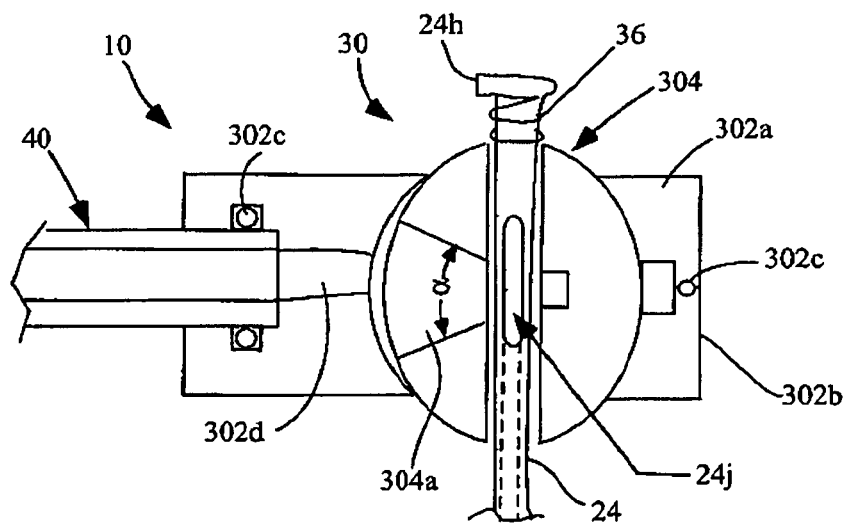
FIG. 24 shows another example of a suspension according to the present invention.

A further modification of the organ manipulation device eliminates the need for tubing 7 altogether, as shown in FIG. 24. In this arrangement, a curved or straight substantially rigid tube 40 is directly connected at its proximal end to a vacuum line leading to a source of vacuum. The rigid tube 40 is leak proof and delivers the vacuum from its proximal end to suspension 30. Suspension 30 is of a modified ball and socket construction, with the socket component 302 being of two piece construction, having an upper portion 302a and a lower portion 302b. The upper and lower portions are brought together on opposite sides of ball 304 to encapsulate it and provide bearing surfaces against which the ball 304 can rotate. The upper and lower portions 302a, 302b are clamped bolted or otherwise compressed together to form an airtight seal with the assistance of O-rings 302c. The upper and lower portions 302a, 302b by this action also tightly clamp support arm 40 so that at least free rotation between support arm 40 and suspension 30 is not possible. The assembled socket component 302 further defines an annular space surrounding ball 304 to ensure that the flow path of the vacuum is not interrupted through a 360 degree rotation of the ball 304 in the horizontal plane.

Ball 304 is provided with a wedge shaped cut out 304a that mates with annular space 302d for fluid connection between the ball 304 and socket 302. The angle α of wedge is at least as great as the angle defining the maximum amount of swing that suction member can rotate about an axis perpendicular to the page on which FIG. 24 appears. This ensures that fluid contact will not be broken even when the suction member swings by a maximum amount, regardless of the amount of rotation in the horizontal plane that has occurred in the ball. Connecting shaft 24 is provided with a slot 24j or other opening that fluidly connects the suction member 20 with the suspension 30. Shaft 24 is freely rotatable with respect to ball 304 about the longitudinal axis of shaft 24. A biasing member 36 (such as a coil spring, for example) is provided between upper stop 24h and ball 304 to allow a limited amount of translation of the suction member 20 with respect to ball 304 and to return the suction member and organ to a desired position of the shaft 24 with regard to ball 304.

Figure 25:
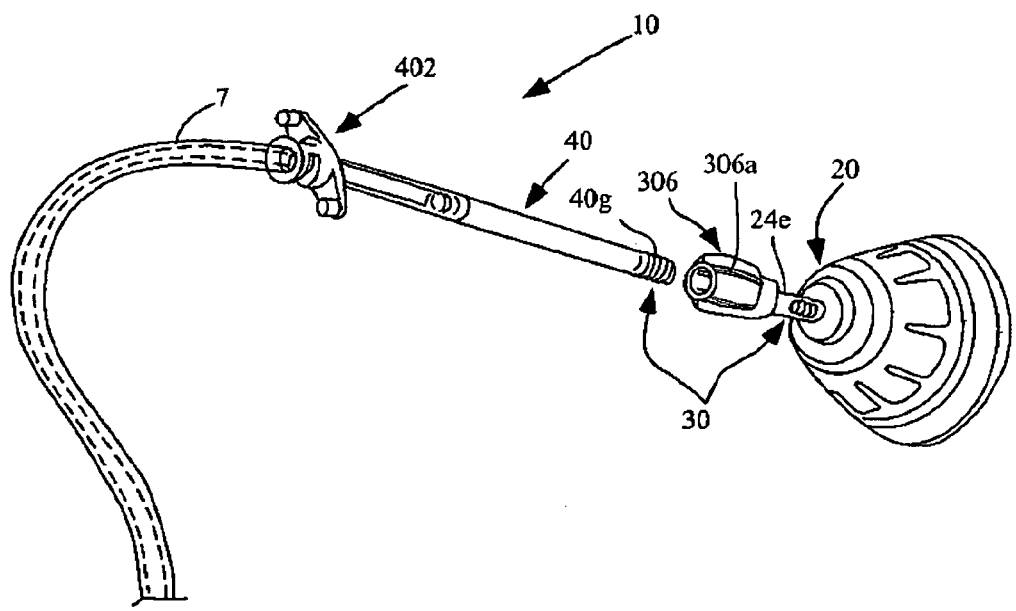
FIG. 25 is an example of an organ manipulation apparatus that is well-suited for intercostal insertion of the supporting shaft.

The organ manipulation apparatus shown in FIG. 25 not only eliminates the need for a vacuum tubing to be run all the way to the site of the suspension (since support arm 40 carries out the function), but allows placement of the suction member against an organ to be manipulated, prior to attaching the support arm. This configuration is particularly adapted for an intercostal or endoscopic delivery of the support arm 40. Suction member 20 may be introduced against the surface of the heart, for example, after having been inserted through another opening, such as a sub-xyphoid incision, for example. Support arm 40 may next be inserted through an intercostal incision in line with the placed suction member 20. A substantially rigid support arm 40 aids in intercostal penetration as well as in connecting the support arm to quick connector 306. Generally, support arm 40 will have a length between about two and eight inches and an outer diameter between about $\frac{1}{8}^{th}$ and $\frac{5}{16}^{th}$ of an inch. Preferably, its diameter matches that of suction line 7. A flexible elastic tubing 24e is preferably used to fluidly connect the quick connector 306 to the suction member to allow flexion close to the heart surface. The distal end portion of support arm 40 is provided with annular grooves 40g which are captured by annular protrusions 306a within quick connector 306, thereby preventing disconnection between the members while at the same time allowing axial rotation of the suction member 24, organ and quick connector 306 with respect to support arm 40. In addition, tube 24e can be adapted to twist or flex to accommodate organ motion.

Figure 26A:
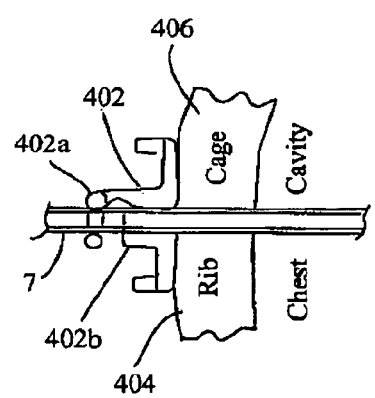
FIG. 26A is a sectional view of a binding member in a freely sliding position.
Figure 26B:
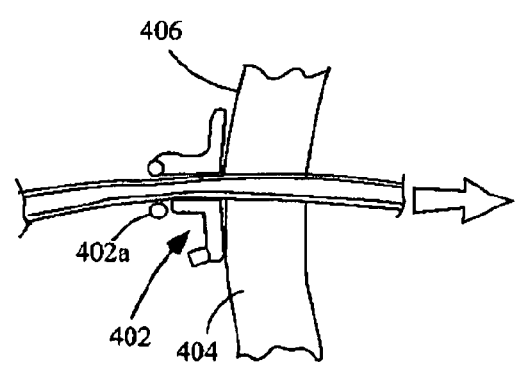
FIG. 26B is a sectional view of the binding member of FIG. 26A, but in the binding position.

A binding member 402 such as a binding ring may be provided to fix a position of the device 10 with respect to the location of insertion of support arm 40, to prevent any further insertion of the tubing into the patient. For example, in an intercostal delivery of support arm 40, binding ring 402 is abutted against the ribs 404,406 between which support arm has been inserted. Prior to connecting up support arm 40 with quick connector 306, the binding leg 402a is maintained substantially in parallel with the main body 402b of the binding ring 402 so that tubing 7 is allowed to slide freely through an opening in binding leg 402a. Once support arm has been properly connected and thus the organ manipulation apparatus is positioned as desired, binding leg 402a is flexed or canted to the locked or frictional position shown in FIG. 26B such that a large amount of force (i.e., a force significantly greater than any forces imposed by the beating heart against the device) is required to overcome the friction imposed by the angled leg 402a against the tubing 7, to move the tubing any further inward into the patient (in the direction of the arrow shown in FIG. 26B).

FIGS. 27A-27E show another example of an organ manipulation apparatus, in various stages of assembly, that may be used to retract an organ prior to mounting to a support arm. Assembly of suction member 20 to suction tube 7 is precluded by sliding a biasing member 36, such as a coil spring, for example, over connecting shaft 24 and then inserting shaft 24 into tube 7 to form an air tight seal either through a friction fit or by gluing or the like. Additionally, the top end of biasing member 36 may be glued to tube 7 in order to facilitate connection of roller 34 to shaft 24, described below. In any case, the outside diameter of tube 7 is greater than that of biasing member 36, so that the distal end of tubing 7 acts as a stop member against which the proximal end of biasing member 36 abuts.

Biasing member 36 function in conjunction with clevis 32 and roller 34 as the suspension 30 in this arrangement. Clevis 32 is substantially inflexible since biasing member 36 allows limited translator movement of suction member 20 with respect to support arm 40. Roller 34 is configured and functions similarly to previously described rollers 34 except that hole 34b has an opening or aperture 39a that enables connection of the support arm to the suction member subsequently to placement of the suction member against the tissue of the organ to be retracted, application of suction to Grasp the tissue, and retraction of the organ. Similar to the embodiment of FIGS. 19A and 19B, aperture 39a of roller 34 defines a gap that is slightly shorter than the outside diameter of shaft 24. The circumference of the hole 34b, however, is slightly greater than the circumference of shaft 24. Connector 32c is rotatably connected to support arm 40, so that clevis 32 can rotate about the longitudinal axis of support arm 40 with respect to support arm 40 after connection thereto. Roller 34 can also axially rotate with respect to levis 32.

To connect roller 34 with shaft 24, roller 34 is approximated with shaft 24 by manipulating support arm to bring the roller into contact with shaft 24, as shown in FIGS. 27D-27E. Pressure is applied such that the beveled aperture 39a slightly squeezes shaft 24 so that it becomes momentarily slightly oval in cross section, just enough for it to squeeze through the aperture 39a. Upon entering and centering itself in hole 34b, shaft 24 resumes it circular cross section and is free to rotate with respect to the roller 34. Roller 34 is mounted onto shaft 24 distally to biasing member 36, which abuts against roller 34 as a lower stop.

Support Arm

As noted above, the organ manipulation devices according to the present invention may use a variety of different types of support arms including, but not limited to solid, substantially rigid straight or curved members, curved or straight tubular members and multi-jointed members, such as those shown in FIGS. 1A and 1B, for example. A primary function of any support arm used is to provide a substantially stationary support for maintaining gross positioning of a retracted organ. A suspension as described herein then connects a suction member to the support arm in a manner which allows some movements of the organ attached to the suction member, while maintaining the organ in the same gross position.

FIGS. 28A-28E show variations of depressible disks and balls (FIG. 28B) that may be used to construct a support arm 40 as shown in FIG. 1A. Since the working space provided by the incision opening is quite limited, it is desirable to make the organ manipulation device 10 as small and low profile as possible to maintain maximum working space, as well as visibility for the surgeon. The device shown in FIG. 1A includes a low profile mount 44 which is connected at a proximal end portion of the support arm 40. The mount includes a first mount portion and a second mount portion, which is pivotally connected to the first mount portion, as shown and described in co-pending application Ser. No. 09/769,904. The first mount portion may be integral with a male articulating surface of a rotational joint that it then forms a part of at the proximal end of the support arm 40. The second mount portion is pivotal away from the first mount portion to position the mount over a fixed object, such as rail 418 or crossbar 5 to release the mount from the fixed object. The mount portion also allows the organ manipulation apparatus 10 to be slid along rail 418 to which it is mounted. The second mount portion is pivotable toward the first mount portion to fix the mount on the fixed object.

The mount 44 may further comprise a locking mechanism adapted to lock the second mount portion to the first mount portion in a closed position upon pivoting the second mount portion toward the first mount portion. The closed position is configured to lock the mount on the fixed object. The fixed object may be a sternal retractor, for example, or other object, which is stationary relative to the moving tissue. The mount portions may each further include a rail grip adapted to engage one side of a rail 418 on a sternal retractor. The locking mechanism may include a living hinge formed in one of the first and second mount portions and a pin extending transversely on the other of the first and second mount portions, the pin being adapted to snap fit into the living hinge.

A cable passes internally through each of the articulating joints formed by depression disks 46 and balls 48 and mount 44. The cable is further attached to a tensioning mechanism proximally of the mount 44. The tensioning mechanism may include a screw mechanism and a knob. The screw mechanism has a first threaded component having a first set of threads and a second threaded component having a second set of threads adapted to mate with the first set of threads. The first threaded component is fixed to the cable and the knob is adapted to torque the second threaded component with respect to the first threaded component. The screw mechanism is adapted to lock the first and second mount portions together in the closed position, to securely lock the organ manipulation apparatus 10 on the rail 418, crossbar 5 or other stationary object on which it is mounted.

The second threaded component may include a torque limiter having a unidirectional slip clutch, which is engageable with the knob 50. The knob 50 positively engages the torque limiter for unthreading the second set of threads from the first set of threads, and positively engages the torque limiter for threading the second set of threads on the first set of threads until a predetermined amount of torque is required to further tension the cable. Upon reaching the predetermined amount of torque during threading, the torque limiter slips with respect to the knob.

The slip clutch may include at least one fin extending from an outer surface of the second threaded member at an angle to a line normal to a tangent line passing through the location from which the fin extends. Each fin is adapted to engage a groove formed in an inner surface of the knob.

The cable includes a stop member fixed to a distal end thereof, such that, upon applying tension to the cable with the tensioning member, the stop member and the tensioning member apply a compressive force to the mount 44, depression disks 46 and balls 48, thereby locking every joint into an assumed orientation.

A coupling mechanism which links the stop member to the connector 32*c*, thereby also linking the support arm 40 to the suspension 30, is further provided. The coupling member may be adapted to lock the connector 32*c* absolutely, or alternatively to capture the connector 32*c* while still allowing it to rotate with respect to the support arm 40, when the cable is placed under a sufficient tension to lock the maneuverable arm. The coupling mechanism may include a socket member rotatably joined with the stop member and adapted to receive the ball of connector 32*c* to form a ball joint. The socket member may further include a slot through a side wall thereof, which terminates in an enlarged opening dimensioned to permit the ball member to pass therethrough. The coupling mechanism may further include a coupling link having arms adapted to lock with the socket member, and an upper abutment surface adapted to abut the stop member. A second coupling link having driving surfaces adapted to contact a distal most link of a distal most articulating joint of the maneuverable arm may also be provided. The second coupling link may further include a lower abutment surface adapted to abut an upper portion of the ball member, wherein, upon tensioning of the cable, the stop member draws the first coupling link and the socket member in a proximal direction, whereby the socket member compresses the ball member against the lower abutment surface. Optionally, a flexible sleeve mall be positioned over the articulating joints of the support arm 40.

Depression disks 46 are threaded over the cable in an alternating series with balls 48. The depression disks 46 are made of a material which is harder than the material from which balls 48 are made. Depression disks have concave surfaces on both sides and are provided with features that are designed to deform portions of abutting balls 48 on either side when the disks 46 and balls 48 are compressed together as the cable is tensioned. This deformation enhances the locking function between each ball and disk, as it is much more difficult to rotate the interlocking surfaces when they are not uniformly spherical. When the tension is released from the cable, the support arm goes from a locked state to a malleable state again as the disks and balls are allowed to separate from one another again, thereby freeing them up to move with respect to one another along the articulating joints. The deformations on the balls also relax when the balls 48 separate from compression by the disks 46, as they are generally made of polymers which are only elastically deformed during the compression/locking phase.

The depression disk 46 shown in FIG. 28A includes grooves or recesses 46*b* which allow the abutting ball 48 to become partially embedded therein during compression due to the tensioning of the cable. FIG. 28B shows an example of a ball 48 which is the basic configuration for use with all of the variations of depression disk 46 shown. Each ball has a conically shaped void 48*a* formed therein that allows angulation of the articulating joint formed between ball 48 and disk 46, by relative rotation of their mating surfaces, without deflecting the cable which runs through both components, thereby maintaining the amount of tension in the cable existing before the articulation. Exemplary material pairs that math be used for the ball 48 and disk 46 to ensure that the disk material is harder than the ball material include: machined polycarbonate ball with machined Ultem disk; molded Isoplast ball with molded polycarbonate/Teflon glass disk; and molded polycarbonate ball with molded Ultem disk.

The depression disk 46 shown in FIG. 28C includes protrusions 46*c* which dig into the abutting ball 48 and form depressions therein, thereby become partially embedded in the ball during compression due to the tensioning of the cable. The protrusion features 46*c* act as grasping features that, upon digging into the surface of the ball 48, increase the force required to deflect the support arm 40 over that required of an arm that is fixed based only on friction between the concave surfaces of the disks and convex surfaces of the balls, thereby increasing the rigidity of support arm 40 in the locked or compressed state. In both disk variants of FIGS. 28A and 28C, the radially oriented features 46*b*/46*c* provide increased resistance to rotational failure of the locking between articulating joint surfaces.

The depression disk 46 shown in FIG. 28D includes circumferentially oriented protrusions 46*d* which dig into the abutting ball 48 and form depressions therein, thereby become partially embedded in the ball during compression due to the tensioning of the cable. The protrusion features 46*d* act as grasping features that, upon digging into the surface of the ball 48, increase the force required to deflect the support arm 40 over that required of an arm that is fixed based only on friction between the concave surfaces of the disks and convex surfaces of the balls, thereby increasing the rigidity of support arm 40 in the locked or compressed state. Circumferentially oriented protrusions 46*d* are radially spaced from each other and provide resistance to rotational failure in a direction normal to that of the resistance provided by the two previously discussed configurations. The resistance provided in this embodiment is in a direction against the tendency of a support arm 40 to sag due to gravitational forces, especially at the distal end of the arm that is not fixed to a stationary object. It is further noted that various combinations of the features shown in FIGS. 28A, 28C and 28D may be employed in a depression disk. For example, a depression disk may include circumferentially oriented protrusions 46*d* with radially oriented recesses 46*b*. Still further, a depression disk may be formed to have circumferentially oriented recesses.

Figure 28E:
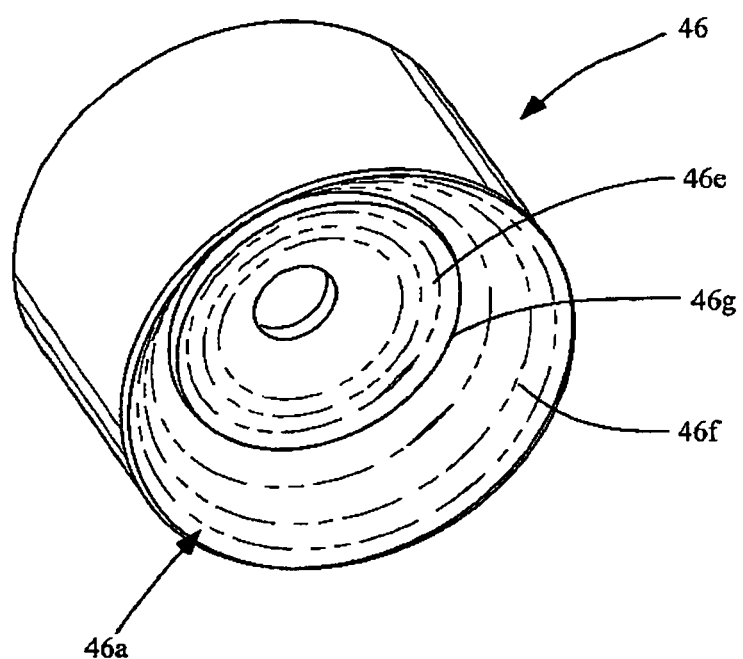
FIG. 28E shows another example of a depression disk that may be used in the articulating arm shown in FIG. 1.
Figure 29:
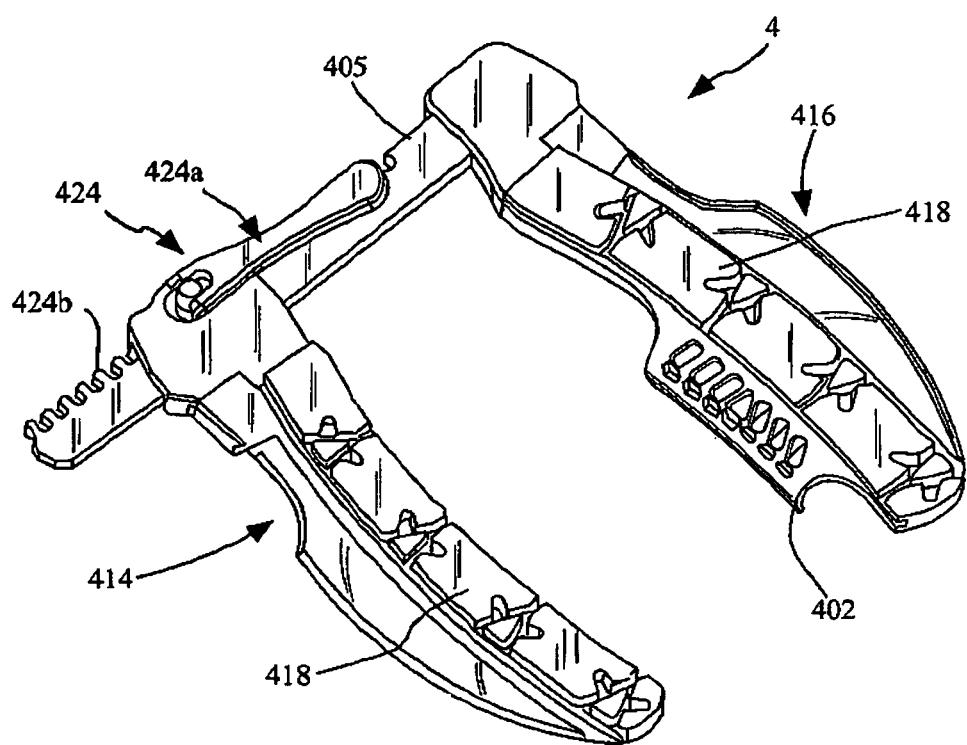
FIG. 29 is a perspective view of a sternal retractor to which an organ manipulation device may be mounted according to the present invention.

The depression disk 46 shown in FIG. 28E is formed of two different materials. The material 46*e* located in the more central portion of the disk and concave surface 46*a* is relatively softer that the material 46*f* located radially outward thereof, on the outer portion of the concave surface 46*a* and depression disk 46. The harder material 46f provides structural support for the disk 46. The softer material 46e, although having a generally concave surface, extends outwardly slightly from the concave surface of the harder material 46f, thereby forming a step or discontinuity where the two materials meet at 46g. When the cable is placed under tension to compress the disk and ball components together, ball 48 compresses the soft material 46e until ball 48 contacts the harder surface 46f. By compressing the softer material 46e, a better, more conforming surface contact with the ball 48 is achieved, thereby increasing the level of friction between surface 46e and ball 48 and between ball 48 and disk 46 overall. The result is increased rigidity of the support arm 40 I the locked state, as compared to a conventional ball and disk arrangement. The soft material 46e must be softer than the material of the ball 48, while the hard material may be of the same hardness as the ball. It is further noted that various combinations of the features shown in FIGS. 28A, 28C and 28D may be employed in a depression disk that also includes the features described with regard to FIG. 28E. For example, a depression disk may include circumferentially oriented protrusions 46d on the surface 46f.

While the present invention has been described with reference to the specific embodiments thereof, it should be understood by those skilled in the art that various changes may be made and equivalents may be substituted without departing from the true spirit and scope of the invention. Just as an example, it is noted that an organ manipulation device, such as shown in FIG. 1 could be modified to replace the connector 44 with a connector 142 of the type shown in FIG. 1 without departing from the true spirit and scope of the invention, and this is only one example, as many such substitutions or modifications are contemplated. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An organ manipulation apparatus comprising:
    a suction member comprising a shaft, wherein the suction member is configured to exert sufficient force on an organ to move the organ when the suction member is placed against the organ, a relative negative pressure is established in a space between the suction member and the organ, and the suction member is moved;
    a support structure capable of being substantially rigidly fixed to a relatively immovable object; and
    a suspension interconnecting said suction member and said support structure, said suspension allowing at least a limited amount of rotation of said suction member with respect to said support structure to accommodate natural movements of the organ;
    wherein said suspension comprises a roller rotatably mounted to a base member and coupled to the shaft, said roller comprising an elongated body with a longitudinal axis of rotation substantially perpendicular to a length of said shaft.

2. The apparatus of claim 1 wherein said suspension further allows a limited amount of translation of said suction member, in a direction along an axis of said shaft, with respect to said support structure.

3. The apparatus of claim 1, further comprising a tubular member in fluid connection with said suction member, wherein the tubular member is adapted to fluidly connect said suction member with a vacuum source.

4. The apparatus of claim 3, wherein the tubular member is a flexible tubular member, and a spring is located along a length of said flexible tubular member.

5. The apparatus of claim 1, wherein the support structure includes an articulating arm capable of assuming a flexible state and a rigid state, said articulating arm comprising a cable; a plurality of depression disks and balls alternatively threaded over said cable, each of said depression disks comprising a pair of concave surfaces adapted to engage a pair of said balls; and a tensioning mechanism adapted to apply tension to said cable, wherein upon application of tension to said cable, said balls and depression disks are compressed against one another and said articulating arm assumes said rigid state.

6. The apparatus of claim 1, wherein said suction member is configured as a cup, said cup comprising an inside surface and an outside surface and a periphery for contacting a surface of the organ, wherein at least a portion of said periphery is lined with foam to form a seal with a surface of the organ.

7. The apparatus of claim 1, wherein said suction member comprises a silicone cup and a foam member located within an interior surface of the silicone cup.

8. The apparatus of claim 1, wherein said suction member comprises a cup formed from an air impermeable material, a first foam layer adjacent an inner surface of the cup; a second foam layer adjacent a periphery of said cup; and a tube in fluid communication with said first foam layer.

9. The apparatus of claim 1, wherein said suction member is constructed from an air impermeable material and has a concave configuration comprising an inner surface and an outer surface, wherein the suction member has at least one opening therethrough for fluidly connecting a vacuum tube to said inner surface, and a foam member adjacent said inner surface and surrounding said vacuum tube.

10. The apparatus of claim 1, wherein said suction member comprises a compliant seal within a perimeter thereof, said compliant seal comprising a substantially flat flange and being deformable to conform to the shape of a surface of the organ upon contact therewith.

11. The apparatus of claim 1, wherein the base member is configured as a clevis and connected to the support structure.

12. The apparatus of claim 1, wherein base member comprises two arms spaced apart from one another and wherein the roller is rotatably connected to the two arms.

13. The apparatus of claim 1, wherein the suction member comprises three degrees of freedom, such that the suction member is movable in three different directions with respect to the support structure.

14. The apparatus of claim 1, wherein the suction member is spring biased to allow translation of the suction member in a direction along the axis of the shaft.

15. The apparatus of claim 14, wherein a spring is located about the shaft to allow translation of the suction member in a direction along the axis of the shaft.

16. The organ manipulation apparatus of claim 1, further comprising friction enhancing features located on the base member that facilitate manipulation of the suspension allow the suspension.

17. An organ manipulation apparatus comprising:
    a suction member comprising a substantially rigid shaft, wherein the suction member is configured to exert sufficient force on an organ to move the organ when the suction member is placed against the organ, a relative negative pressure is established in a space between the suction member and the organ, and the suction member is moved;

a support structure adapted to be substantially rigidly fixed to a relatively immovable object; and a suspension interconnecting said suction member and said support structure, said suspension allowing at least a limited amount of rotation of said suction member with respect to said support structure to accommodate natural movements of the organ;

wherein said suspension comprises a roller rotatably mounted in a base member, said roller comprising an axis of rotation and a bore substantially perpendicular to said axis of rotation, said substantially rigid shaft being mounted in said bore.

18. A surgical method performed on a beating heart using a manipulation device, wherein the manipulation device comprises:

a suction member comprising a shaft;

a support arm; and a suspension interconnecting said suction member and said support arm, wherein said suspension comprises a roller, said roller comprising an elongated body with a longitudinal axis of rotation substantially perpendicular to a length of said shaft, and wherein the surgical method comprises the steps of:

securing the suction member of the manipulation device to a surface of the heart through the use of suction;

moving the suction member to retract the heart into a position that provides access to a surgical site that would be difficult or impossible to access without retraction; and fixing the support arm with respect to a stationary object, wherein the suspension permits at least limited translation of the heart and the suction member with respect to the support arm.

19. The method of claim 18, further comprising the steps of:

contacting a surface of the heart with a stabilizer in the vicinity of a surgical target to stabilize the surgical target; and performing a surgical procedure on the surgical target.

20. The method of claim 18, further comprising the step of adjusting a position of the suction member in three different directions with respect to the support arm.

21. The method of claim 18, wherein the step of securing involves securing the suction member to an apex portion of the heart.

22. A system useful for positioning a beating heart during a performance of beating heart coronary artery bypass grafting, said system comprising:

an organ manipulation device, wherein the organ manipulation device comprises:

a suction member comprising a shaft, wherein the suction member is configured to exert sufficient force on the beating heart to move the beating heart when the suction member is placed against a surface of the heart and a relative negative pressure is established in a space between the suction member and the heart;

a support structure adapted to be substantially rigidly fixed to a relatively immovable object; and a suspension interconnecting said suction member and said support structure, said suspension allowing at least a limited amount of rotation of said suction member with respect to said support structure to accommodate natural movements of the beating heart, wherein said suspension comprises a roller rotatable mounted to a base member and coupled to the shaft in a manner such that the suction member comprises a rotational degree of freedom about an axis of the shaft and a translational degree of freedom in a direction along the axis of the shaft, said roller comprising an elongated body with a longitudinal axis of rotation substantially perpendicular to a length of said shaft.

23. The system of claim 22, further comprising a retractor, and wherein said support structure and said stabilizer are capable of being fixed to the retractor.

24. The system of claim 22, wherein the base member is configured as a clevis and connected to the support structure.

25. The system of claim 22, wherein the suction member comprises has three degrees of freedom, such that the suction member is movable in three different directions with respect to the support structure.

26. The system of claim 25, wherein the suction member further comprises a suction cup and wherein a spring is located about the shaft to allow translation of the suction cup in a direction along to the axis of the shaft.

27. The system of claim 22, wherein the suction member comprises three degrees of freedom such that it is movable in three different directions with respect to the support.

28. The system of claim 22, wherein the suction member further comprises a suction cup and wherein the suction member is spring biased to allow translation of the suction cup in a direction along the axis of the shaft.

29. A system for performing beating heart bypass grafting surgery, the system comprising:

the heart positioning system of claim 22, and a stabilizer device comprising at least one contact member adapted to contact the beating heart at or adjacent a location where an anastomosis is to be performed.

30. An assembly useful for reversibly connecting to an organ during a surgical procedure to movably secure the organ with respect to a relatively immovable object, the assembly comprising:

a suction member comprising a proximal portion, a lip and a sidewall extending therebetween, the suction member configured to exert a force on an organ when the suction member is placed against the organ and a relative negative pressure is established in a space between the suction member and the organ;

a shaft extending proximally from the proximal portion of the suction member; and a suspension assembly, comprising:

an end connector for attaching to a distal end of a support structure;

a first arm extending distally from the end connector;

a roller rotatably supported by the first arm and configured for slidably receiving the shaft to allow for translation of the shaft with respect to the roller, wherein the roller comprises an elongated body with a longitudinal axis of rotation substantially perpendicular to a length of the shaft; and a spring for maintaining a spring force between the suction member and the roller;

wherein the suspension assembly allows at least a limited amount of rotation of said suction member with respect to said support structure to accommodate natural movements of the organ.

31. The assembly of claim 30, wherein the suspension assembly further comprises a second arm extending distally from the end connector, the roller rotatably supported by the second arm.

32. The assembly of claim 31, wherein the first arm and the second arm form a clevis structure.

33. The assembly of claim 31, wherein at least one of the first arm and second arm comprise friction enhancing features.

34. The assembly of claim 30, further comprising tubing connectable to a pressure source for establishing the relative negative pressure, wherein a proximal portion of the shaft is in fluid communication with the tubing.

35. An organ manipulation apparatus comprising:
- a suction member configured to exert sufficient force on an organ to move the organ when the suction member is placed against the organ, a relative negative pressure is established in a space between the suction member and the organ, and the suction member is moved;
- a support structure adapted to be inserted through a small opening in a body of a patient;
- a coupling member into which said support structure is fitted after insertion of said support structure through the small opening; and
- a flexible suspension interconnecting said suction member and said coupling member.

36. The apparatus of claim 35, wherein said flexible suspension comprises a flexible tubular member that allows a limited amount of translation of said suction member in a direction along an axis of said shaft, with respect to said support structure.

* * * * *